United States Patent [19]

Masuda et al.

[11] Patent Number: 5,751,396
[45] Date of Patent: May 12, 1998

[54] OPHTHALMIC APPARATUS INCLUDING OCULAR FUNDUS ILLUMINATING SYSTEM FOR ILLUMINATING THE FUNDUS OF THE EYE TO BE EXAMINED THROUGH THE PUPIL THEREOF

[75] Inventors: Takashi Masuda, Yamato; Kyoji Sekiguchi; Toshiaki Okumura, both of Yokohama; Hiroshi Aoki, Kawasaki; Osamu Yamamoto, Yokohama, all of Japan

[73] Assignee: Canon Kabushiki Kaisha, Tokyo, Japan

[21] Appl. No.: 826,536

[22] Filed: Apr. 2, 1997

Related U.S. Application Data

[63] Continuation of Ser. No. 149,922, Nov. 10, 1993, abandoned.

[30] Foreign Application Priority Data

Nov. 10, 1992 [JP] Japan .................... 4-324949

[51] Int. Cl.⁶ .................................................. A61B 3/10
[52] U.S. Cl. ............................................ 351/221; 351/208
[58] Field of Search ................................... 351/221, 208, 351/211, 212, 245

[56] References Cited

U.S. PATENT DOCUMENTS

| | | |
|---|---|---|
| 4,572,627 | 2/1986 | Madate et al. . |
| 4,690,525 | 9/1987 | Kobayashi et al. . |
| 4,710,003 | 12/1987 | Masuda et al. . |
| 4,762,410 | 8/1988 | Sekiguchi et al. ............. 351/206 |
| 4,764,006 | 8/1988 | Hamano et al. . |
| 4,878,750 | 11/1989 | Sekiguchi . |
| 5,270,749 | 12/1993 | Okumura ......................... 351/221 |
| 5,455,644 | 10/1995 | Yazawa et al. ................. 351/206 |

FOREIGN PATENT DOCUMENTS

| | | |
|---|---|---|
| 2302243 | 12/1990 | Japan . |
| 496730 | 3/1992 | Japan . |

*Primary Examiner*—William L. Sikes
*Assistant Examiner*—James A. Dudek
*Attorney, Agent, or Firm*—Fitzpatrick, Cella, Harper & Scinto

[57] ABSTRACT

This invention provides an ophthalmic measuring apparatus and an ophthalmic apparatus particularly for observation by retroillumination. The ophthalmic measuring apparatus is provided with an eye measuring system, an observing system enabling observation of the eye to be examined by the examiner, an anterior segment illuminating system and a control system. The ophthalmic apparatus is provided with an observing system enabling observation of the eye to be examined, an ocular fundus illuminating system, a time measuring means and a control system.

37 Claims, 21 Drawing Sheets

| FIG. 13A |
| FIG. 13B |

FROM FIG. 13A

| FIG. 18A |
|----------|
| FIG. 18B |

5,751,396

OPHTHALMIC APPARATUS INCLUDING OCULAR FUNDUS ILLUMINATING SYSTEM FOR ILLUMINATING THE FUNDUS OF THE EYE TO BE EXAMINED THROUGH THE PUPIL THEREOF

This application is a continuation of application Ser. No. 08/149,922 filed Nov. 10, 1993, now abandoned.

BACKGROUND OF THE INVENTION

1. Field of the Invention

The present invention relates to an ophthalmic measuring apparatus and an ophthalmic apparatus, adapted for use in the ophthalmic therapy or the like.

2. Related Background Art (a) The conventional eye refractometer is provided with an observing optical system for observing the anterior segment of the eye and a measuring optical system independent from the observing optical system, and the alignment between the eye to be examined and the apparatus is achieved by the examiner through a CRT monitor incorporated in the apparatus.

(b) The Japanese Patent Laid-open Application No. 2-302243 discloses an ophthalmic apparatus for employing observation by retroillumination, utilizing the light beam reflected by the ocular fundus.

(c) The conventional eye refractometer project a target onto the fundus of the eye to be examined, stores the reflected image of the ocular fundus into an image memory, determines the refractive power of the eye by calculation process, and displays the determined refractive power on a display unit for the observation of the anterior part of the eye, provided in the apparatus. Also, there is provided a switch for displaying the reflected image of the ocular fundus stored in the image memory on the display unit in case the examiner judges that the errors occured happens or that the measured value is abnormal during measuring an eye.

(d) The conventional ophthalmic measuring apparatus is generally designed capable of generally retroillumination method, which consists of projecting illuminating light onto the fundus of the eye to be examined, illuminating the lens of the eye by the reflected light and observing the opacity of the lens with a slit lamp or the like.

(e) Also the Japanese Patent Laid-open Application No. 4-96730 discloses an ophthalmic measuring apparatus provided with a system for observing the anterior segment of the eye and a system for observing the image by retroillumination, and capable of switching the observing mode.

(f) Furthermore, the Japanese Patent Laid-open Application No. 4-96730 discloses an ophthalmic measuring apparatus capable of detecting the amount of displacement of the observing position of an optical system for observing the lens of the eye to be examined by retroillumination.

FIG. 1 shows a conventional anterior segment of the eye observing optical system designed to observe the image by retroillumination, wherein, on an optical path from a light source 1 to an eye to be examined E, there are provided an aperture 2, a dichroic mirror 3, a lens 4 and a dichroic mirror 5. Also on an optical path behind the dichroic mirror 5, there are provided a lens 6, a dichroic mirror 7, a lens 8 and an imaging device 9. Also on an optical path in a direction of light reflected by the dichroic mirror 3 there are provided an aperture 10 and a light source 11 for retroillumination of the image. On an optical path in a direction of light reflected by the dichroic mirror 7, there are provided a lens 12, an annular target 13 for alignment, and a light source 14. The dichroic mirror 5 has a property of transmitting a part of wavelength of the light emitted by the light source 1 and reflecting the rest part of wavelength thereof.

The light from the light source 1 is transmitted through the aperture 2, constituting a fixation target, and illuminates the cornea Ec of the eye to be examined E by way of the lens 4 and the dichroic mirror 5. A part of the light beam reflected on the surface of the cornea Ec is transmitted through the dichroic mirror 5, then guided through the lens 6, the dichroic mirror 7 and the lens 8 and projected as a corneal reflected image on the imaging device 9. The light from the light source 14 illuminates the target 13, then guided through the lens 12, the dichroic mirror 7 and the lens 8, and focused as an annular alignment image on the imaging device 9.

The corneal reflected image and the annular alignment image on the imaging device 9 are displayed on an unshown monitor. The examiner achieves alignment, while observing the monitor, by moving the main body of the apparatus in such a manner that the corneal reflected image becomes positioned inside the annular of the alignment image in the vertical and lateral directions, and in such a manner that the corneal reflected image becomes sharpest in the axial direction.

The displacement of the optical system is detected, as the displacement of an unshown sliding mechanism consisting of a movable table supporting the main body of the apparatus and a fixed table movable relative thereto.

SUMMARY OF THE INVENTION

In view of the conventional arts explained above, the present invention is to provide a excellent apparatus in practical use in the ophthalmic measuring and in the ophthalmic apparatus designed particularly for observation by retroillumination.

The object of a first invention of this application is to provide an ophthalmic measuring apparatus for observation by retroillumination, capable of selecting whether simultaneous observation of the image of the anterior part of the eye is employed or not.

The object of a second invention of this application is to provide an ophthalmic measuring apparatus for observation by retroillumination, capable of avoiding the burden and hazard and the like to the eye to be examined.

The object of a third invention of this application is to provide an ophthalmic measuring apparatus, capable of applying a process to the image of the pupil area, namely a process for output to an external equipment.

The object of a fourth invention of this application is to provide an ophthalmic apparatus, capable of more precisely controlling the conditions of observation by retroillumination.

The object of a fifth invention of this application is to provide an ophthalmic apparatus, capable of effecting the observation by retroillumination with illumination control.

The object of a sixth invention of this application is to provide an ophthalmic measuring apparatus, capable of observing the pupil area of the eye to be examined and simultaneously measuring characteristic of the eye to be examined in continuous manner, thereby easily finding a measurable area of the ocular fundus even if the eye to be examined shows cataract.

The object of a seventh invention of this application is to provide an ophthalmic measuring apparatus capable of easily ascertaining the abnormal result by failure the measurement of the predetermined information of the eye to be examined, thereby providing a highly reliable measured value even if the eye to be examined shows cataract.

The object of an eighth invention of this application is to provide an ophthalmic measuring apparatus, enabling observation by retroillumination without excessive illumination on the eye to be examined, and also enabling observation with an optimum magnification in each of the retroillumination observation mode and the anterior segment of the eye observation mode.

The object of a ninth invention of this application is to provide an ophthalmic apparatus enabling easy and precise detection of the amount of displacement of the observing optical system in the ocular fundus, and also enabling easy focusing.

Still other objects of the present invention, and the features thereof, will become fully apparatus from the following description of the embodiments.

DETAILED DESCRIPTION OF THE PREFERRED EMBODIMENTS

Now the present invention will be clarified in detail on the basis of embodiments shown in FIGS. 2 to 35.

Figure 1:
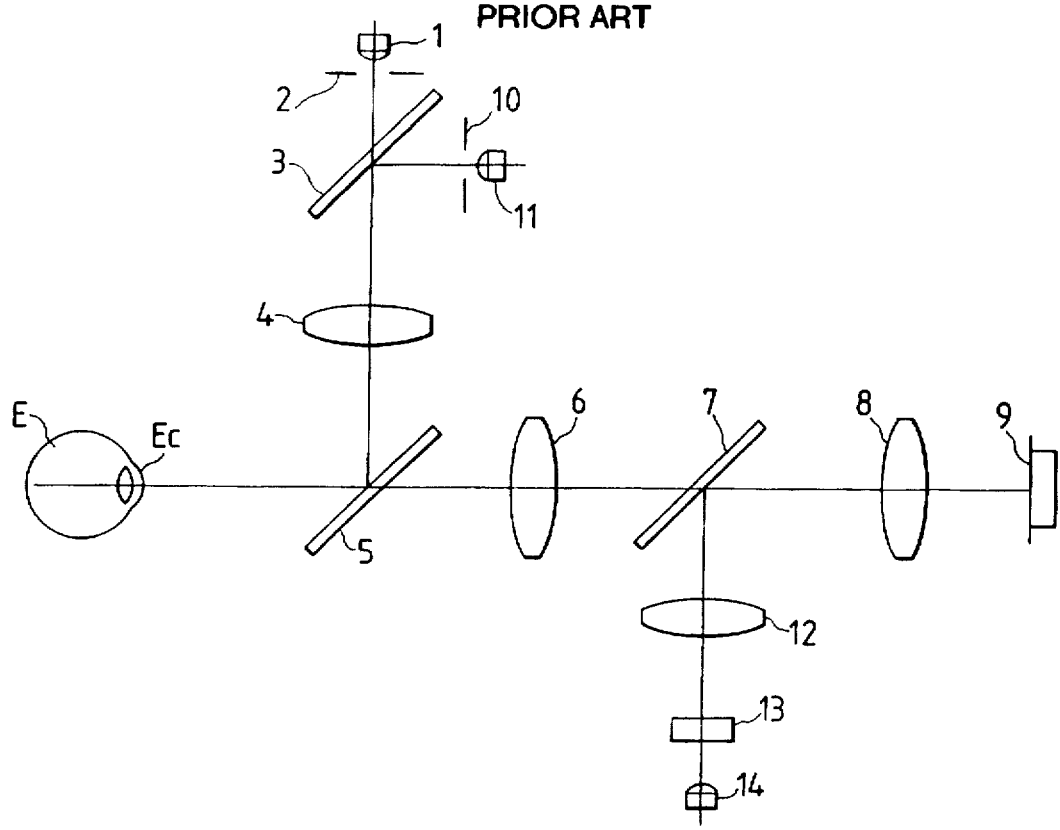
FIG. 1 is a schematic view of shown a conventional embodiment.
Figure 2:
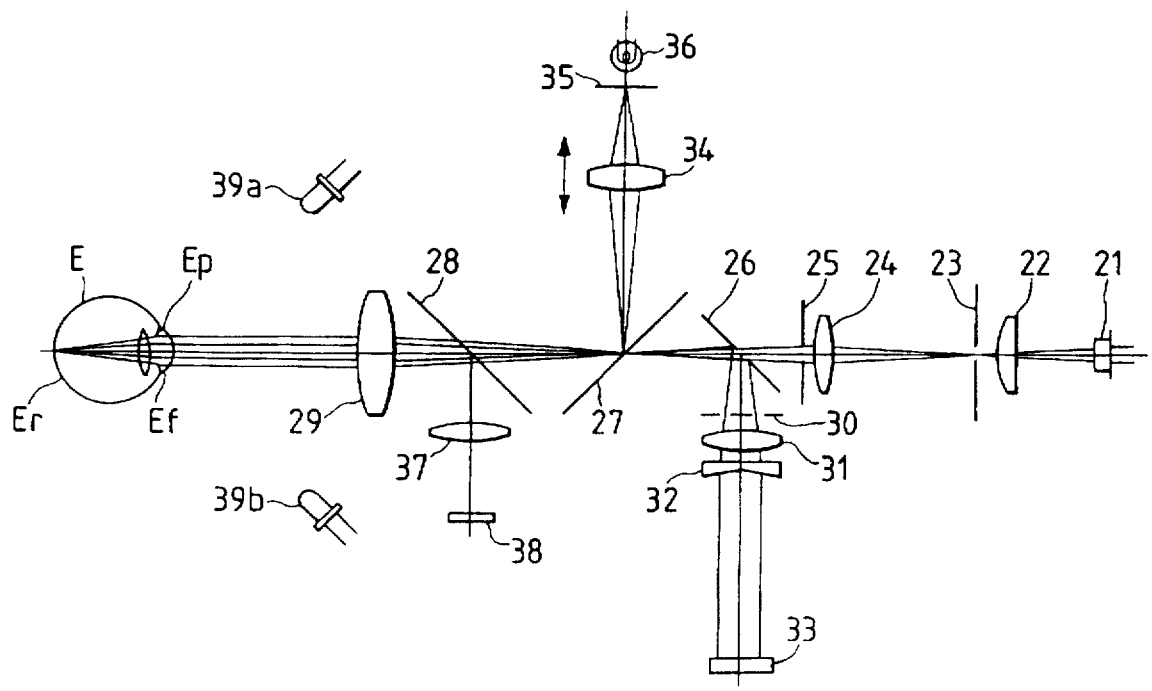
FIG. 2 is a schematic view of a first embodiment.
Figure 3A:
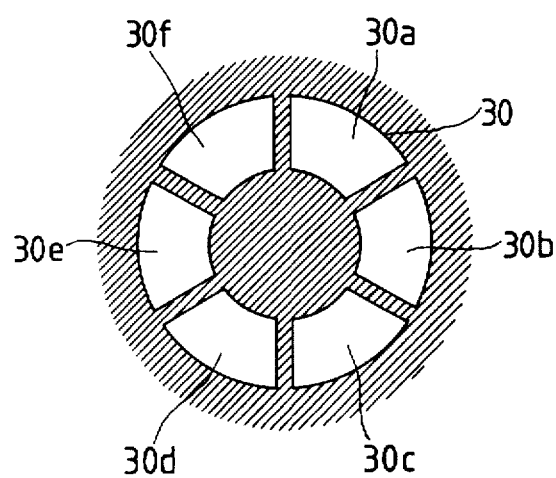
FIG. 3A is an elevation view of an aperture diaphragm.

FIG. 2 illustrates the configuration of a first embodiment of the present invention, wherein, on an optical path from a measuring infrared light source 21 to the eye to be examined E, there are provided a condenser lens 22, a measuring target 23, a relay lens 24, an aperture 25 with a central aperture of a variable diameter, a holed mirror 26, light-splitting members 27, 28, and an objective lens 29. Also on an optical path in the direction of light beam reflected by the holed mirror 26, there are provided a multi-aperture diaphragm 30 having six, apertures 30a–30f as shown in FIG. 3A, a relay lens 31, a splitting prism 32 consisting of six prisms, and an imaging device 33. Also on an optical path in the direction of reflection by the light-splitting member 27, there are provided an axially movable relay lens 34 along the optical path, a fixation target 35 and a light source 36 for emitting visible light for illuminating the visual target. On an optical path in the direction of reflection of the light splitting member 28 there are provided a relay lens 37 and an imaging device 38. Diagonally in front of the anterior segment of the eye Ef there are also provided light sources 39a, 39b for illuminating the anterior segment.

The center-aperture diaphragm 25 and the multi-aperture diaphragm 30 are in optical conjugation with the pupil Ep of the eye to be examined E. The light splitting member 27 has spectral characteristics of reflecting the visible light and transmitting the infrared light, while the light splitting member 28 is coated with a multilayered film for transmitting or reflecting the light beam depending on the wavelength, and has spectral characteristics of reflecting the spectral components of the infrared light and the light beam emitted from the light sources 39a, 39b for illuminating the anterior segment of the eye, while reflecting the light emitted by the measuring light source 21 by a certain proportion, and transmitting the visible light.

The light beams emitted by the light source 39a, 39b illuminates the anterior segment Ef of the eye to be examined E, and the light reflected therefrom is transmitted through the relay lens 29, light splitting member 28 and relay lens 37 and projected on the imaging device 38 as an image of the anterior segment of the eye, which is displayed on an unshown television monitor attached to the main body. The examiner executes the alignment of the apparatus, while observing the television monitor.

The light beam from the fixation target 35 illuminated by the light source 36 is transmitted through the relay lens 34, then reflected by the light splitting member 27, further passed through the light splitting member 28 and the objective lens 29 and projected onto the ocular fundus Er of the eye to be examined E. In the preliminary measurement, the examiner varies the apparent visibility of the fixation target 35 according to the refractive power of the eye to be examined E by moving the relay lens 34, and fixed the line of sight of the eye to be examined E.

Figure 3B:
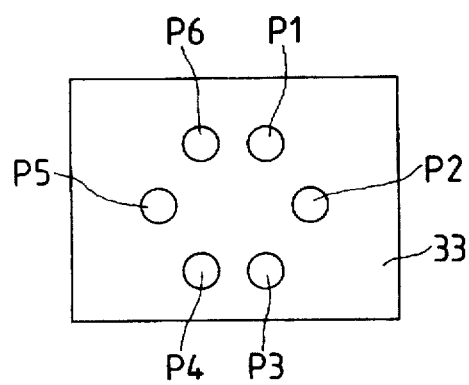
FIG. 3B is a schematic view of an image formed by the reflected light beams, on the imaging device.

The light beam from the measuring light source 21 illuminates the measuring target 23 through the condenser lens 22, and then is projected, through the relay lens 24, center-aperture diaphragm 35, aperture of the holed mirror 26, light splitting members 27, 28 and objective lens 29, onto the ocular fundus Er. The reflected light therefrom illuminates the pupil Ep, then is transmitted through the objective lens 29, and is partly transmitted and partly reflected by the light splitting member 28. The transmitted light beam passes through the light splitting 27, then is reflected by the reflecting face of the holed mirror 26, is transmitted through the apertures 30a–30f of the multi-aperture diaphragm 30 and the relay lens 31, is then splitted and deflected by the separating prism 32 and is focused on the imaging device 33 as six reflected images P1–P6 as shown in FIG. 3B. The refractive power of the eye is calculate d from the coordinates of the center of gravity of the each of the reflected images P1–P6. Also the light beam reflected by the light splitting member 28 is transmitted through the relay lens 37 and projected on the imaging device as an image by retroillumination.

Figure 4:
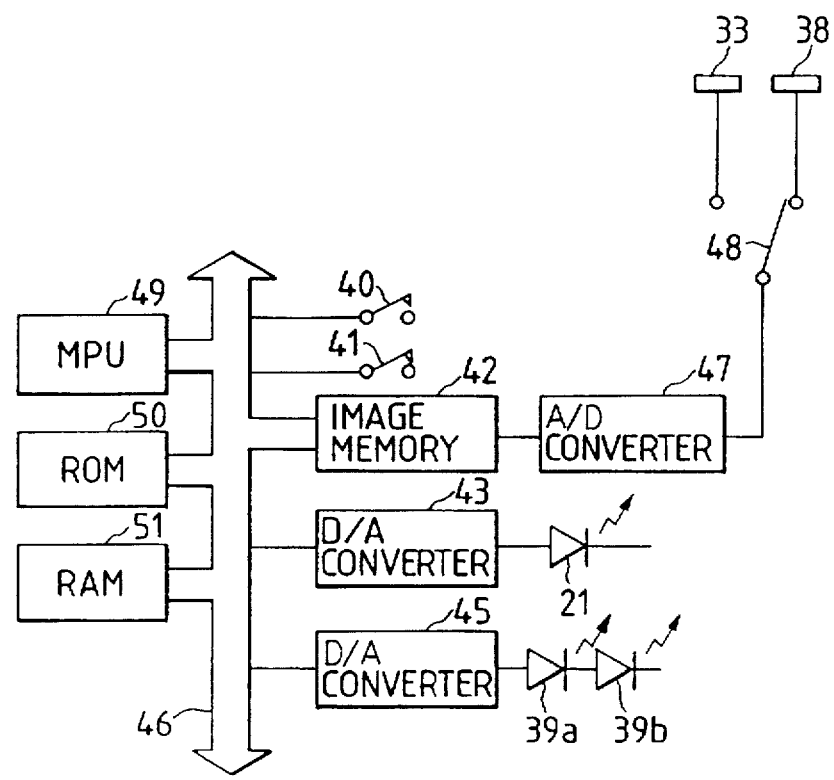
FIG. 4 is a block diagram of electric circuits.

This embodiment is provided with a circuit for turning on and off the light sources 39a, 39b for illuminating the anterior segment of the eye. FIG. 4 is a block diagram of the circuit, in which a measuring switch 40 for starting the measurement of the refractive power of the eye after the alignment against the apparatus, a retroillumination observation switch 41 for turning on and off the measuring light source 21 for observation by retroillumination independently from the switch 40, an image memory 42 for storing digitized video signal, a D/A converter 43 f or varying the intensity of the measuring light source 21, and a D/A converter 45 for controlling the intensity of the light sources 39a, 39b for illuminating the anterior segment of the eye, are connected to a data bus circuit 46. The image memory 42 is connected, through an A/D converter 47 and a switch 48, to the imaging devices 33, 38. The data bus circuit 46 is further connected to an MPU 49, a ROM 50 and a RAM 51.

During measuring of the refractive power of the eye, the light sources 39a, 39b for illuminating the anterior segment of the eye are turned on, and the apparatus is aligned with the eye to be examined E. After the alignment, the measuring switch 40 is actuated to turn on the measuring light source 21 whereby the reflected images P1–P6 are formed on the imaging device 33. The refractive power of the eye is calculated from the positions of the images, and the measured value is displayed on the monitor.

In this embodiment, an area sensor is employed as the imaging device 33 and the refractive power of the eye is calculated from the receiving positions of the light beams reflected at the ocular fundus, but there may be employed another method of measurement of the refractive power. Otherwise the refractive power of the eye to be examined E can be determined with a line sensor or photosensor, by moving the lens or the sensor to a position conjugate with the ocular fundus Er and measuring the amount of the displacement.

For observation by retroillumination of the internal transparent member of the eye to be examined E, the retroillumination observation switch 41 is actuated to continuously turn on the measuring light source 21, whereby the image by retroillumination is formed on the imaging device 38 and is displayed on the monitor. The image of the anterior segment of the eye can be simultaneously observed by turning on the light sources 39a, 39b.

Also in consideration of the protection of the eye to be examined, the MPU 49 may effect such control as to automatically turn off the measuring light source 21 after continuous activation thereof for a predetermined time, according to the time measurement by an internal timer (not shown). In such case, the turn-on time of the light source 21 may be displayed on the monitor for more accurate safety control.

In the above-explained embodiment, the measuring light source 21 is continuously turned on by the switch 41 at the observation by retroillumination, but it is also possible to avoid excessive projection of the light onto the ocular fundus by setting the observation by retroillumination as an operation mode which is entered by the actuation of the switch 41, and turning on the measuring light source 21 only during the pushing of the switch 41.

By entering the output signals of the two imaging devices 33, 38 through the switch 48 and the A/D converter 47 into the image memory 42, there can be memorized the reflected images P1–P6 formed on the imaging device 33 at the eye refractometry, the image of the anterior segment of the eye and the image by retroillumination formed on the imaging device 38. It is furthermore possible to display the images stored in the image memory 42 as still images on the monitor, or to transmit the video signals of the monitor to unshown image recording means such as a still video recorder or a video printer.

Whether to observe and record the image of the anterior segment of the eye such as iris and eyelid and the image by retroillumination at the same time or to observe and record the image by retroillumination only can be selected by controlling the light sources 39a, 39b for illuminating the anterior segment of the eye, by means of the D/A converter 45. Also the MPU 49 judges the density of the image by retroillumination, stored in the image memory 42 (equivalent to the detection of the intensity, at the pupil of the light reflected at the ocular fundus), and accordingly effects controls such as variation of the intensity of the measuring light source 21 and variation of the amplification gain of the imaging device 38. In this manner the image by retroillumination can be observed with a constant brightness, regardless of the presence of cataract or the level of reflectance of the ocular fundus Ef.

Also a change in the diameter of the aperture of the center-aperture diaphragm 25 varies the area of the ocular fundus Er illuminated by the measuring light source 21. Thus, if the observation by retroillumination is difficult due to a very weak reflected light from the ocular fundus Er because of cataract or other desease, the aperture of the center-aperture diaphragm 25 is enlarged to increase the amount of amount entering the eye to be examined E, thereby providing brighter illumination to the pupil Ep and facilitating the observation. In this apparatus, the examiner can enter the necessary illumination intensity by unshown input means, whereby the MPU 49 can control the diameter of the aperture. However, if the aperture is made excessively wide, the incident light beam has a wider area to the pupil Ep whereby the light beam reflected by the cornea Ec tends to return into the objective lens 29, thus inducing an optical noise in the observation by retroillumination. Consequently the diameter of the aperture is preferably so controlled that the light beam reflected by the cornea does not enter the objective lens 29.

The above-mentioned controls for the protection of the eye to be examined E, the image recording and the automatic regulation of the light source are likewise effective, not only in the apparatus for observation by retroillumination, utilizing the light beam of the measuring light source 21 reflected by the ocular fundus, but also in an apparatus equipped with an exclusive light source for the observation by retroillumination, as disclosed in the Japanese Patent Laid-open Application No. 2-302243.

Figure 5:
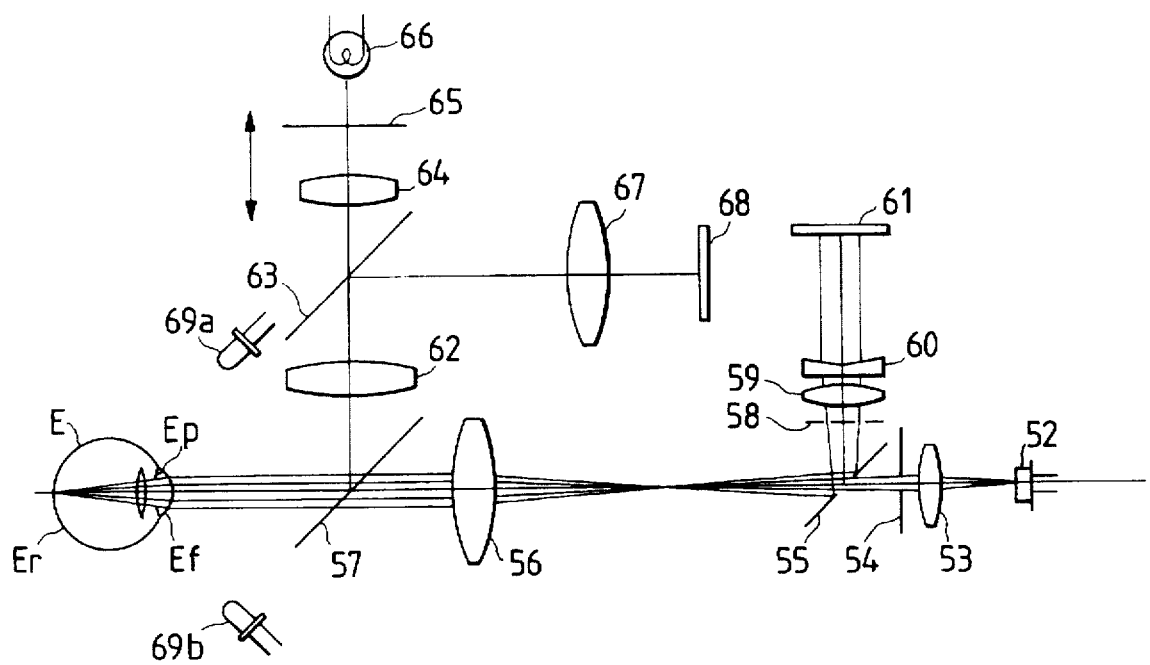
FIG. 5 is a schematic view of a second embodiment.
Figure 6:
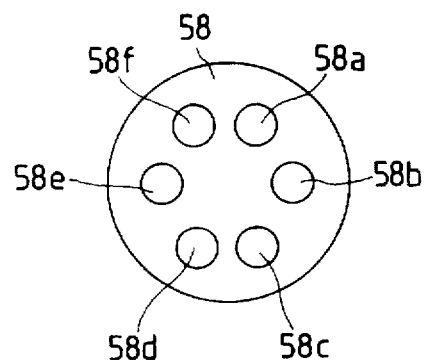
FIG. 6 is an elevation view of a multi-aperture diaphragm.

FIG. 5 shows the configuration of a second embodiment, wherein, on an optical path from a measuring light source 52 to the eye to be examined E, there are provided a lens 53, an aperture 54, a holed mirror 55, a lens 56 and a dichroic mirror 57. On an optical path in the direction of reflection by the holed mirror 55, there are provided a multi-aperture diaphragm 58 having six apertures 58a–58f as shown in FIG. 6, a lens 59, a splitting prism 60 consisting of six prisms, and an imaging device 61. Also on an optical path in the direction of reflection by the dichroic mirror 57, there are provided a lens 62, a dichroic mirror 63, an axially movable lens 64, a fixation target 65 and a light source 66 for illuminating the target 65. In the direction reflection of the dichroic mirror 63 there are provided a lens 67 and an imaging device 68, and, diagonally in front of the anterior segment of the eye Ef there are provided light sources 69a, 69b for illuminating the anterior part. The aperture 54 and multi-aperture diaphragm 58 are positioned in optically conjugate with the pupil Ep.

The light beams from the light sources 69a, 69b illuminate the anterior segment of the eye Ef, and the reflected light beam therefrom is guided through the dichroic mirror 57, lens 62, dichroic mirror 63 and lens 67 and is projected as an image of the anterior segment of the eye on the imaging device 68. The light beam from the light source 66 illuminates the fixation target 65 from the rear, then is guided through the lens 64, dichroic mirror 63 and lens 62, then reflected by the dichroic mirror 57 and projected onto the ocular fundus Er. In this state the visibility of the fixation target 65 is adjusted by moving the lens 64, and the line of sight of the eye to be examined E is fixed.

Figure 7:
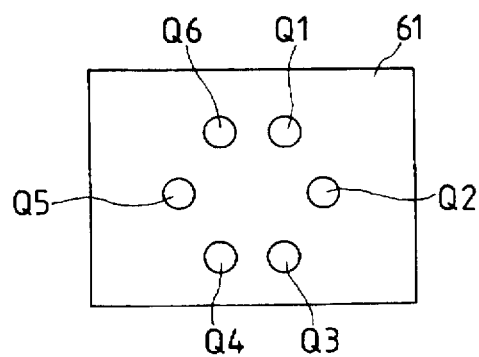
FIG. 7 is a schematic view of an image, formed by measuring light beam projected onto the measuring imaging device.

The light beam from the measuring light source 52 is guided through the lens 53, aperture 54, holed mirror 55, lens 56 and dichroic mirror 57 and is projected onto the ocular fundus Er. The reflected light beam therefrom illuminates the pupil Ep, and is partly transmitted and partly reflected by the dichroic mirror 57. The transmitted light beam is guided through the lens 56, then is reflected by the holed mirror 55, further guided through the multi-aperture diaphragm 58, lens 59 and, splitting prism 60 and is projected, on the imaging device 61, as six reflected circular images Q1–Q6 as shown in FIG. 7. The small circular images Q1–Q6 respectively correspond to the light beams passing through the six apertures 58a–58f of the multi-aperture diaphragm 58, and the refractive power of the eye to be examined E can be determined from the positions of the reflected images Q1–Q6. The measuring light source 52 is turned on only during the eye refractometry.

On the other hand, the light beam reflected by the dichroic mirror 57 is guided through the lens 62, then is reflected by the dichroic mirror 63, and is projected by the lens 67 onto the imaging device 68 as an image by retroillumination.

Figure 8:
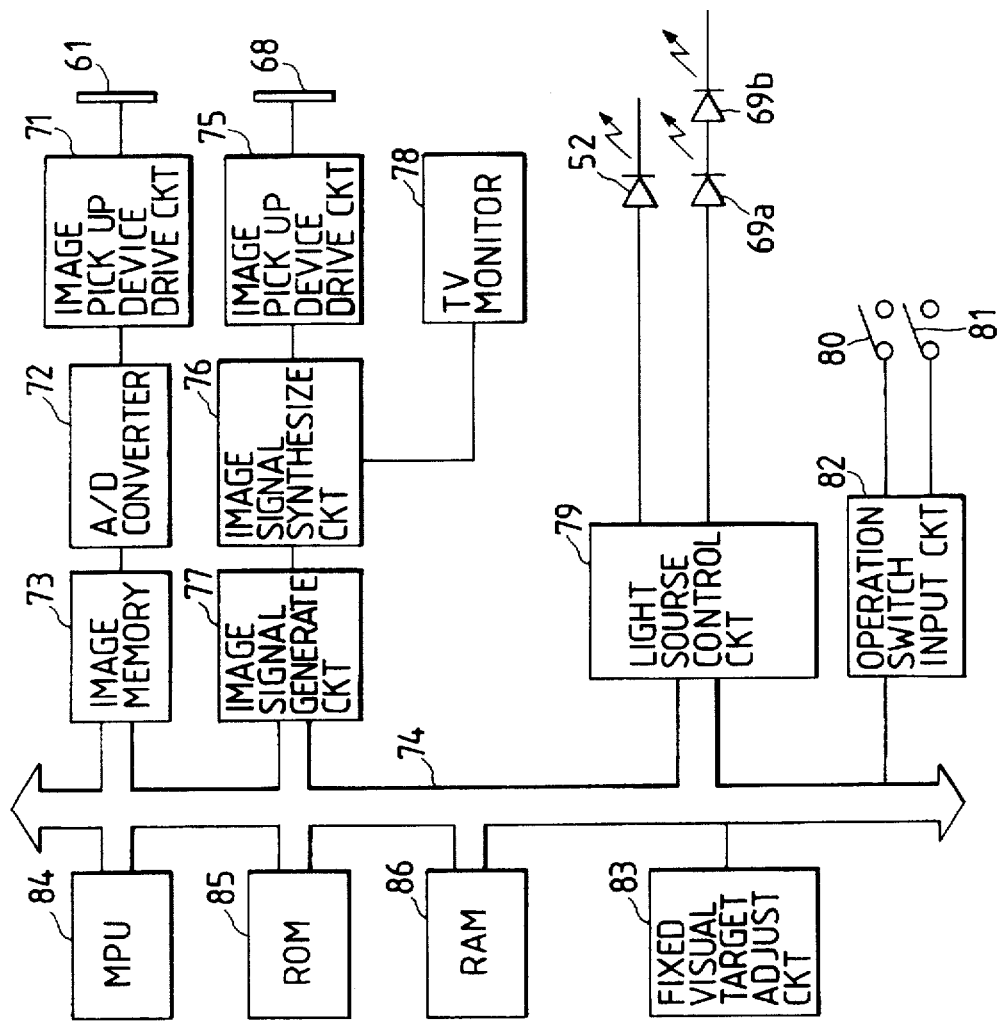
FIG. 8 is a block diagram of electric circuits.

In this embodiment there is provided a circuit for controlling the measuring light beam 52 and processing the measured values, and the block diagram of the circuit is shown in FIG. 8. The imaging device 61 is connected with a data bus circuit 74 through an imaging device driving circuit 71, an A/D converter 72 and an image memory 73, while the imaging device 68 is connected to the data bus circuit 74 through an imaging device driving circuit 75, an image signal synthesis circuit 76 and an image signal generation circuit 77. The output of the image signal synthesis circuit 76 is supplied to a television monitor 78. The measuring light source 21, and the light sources 69a, 69b for illuminating the anterior segment of the eye are connected to the data bus circuit 74 through a light source control circuit 79, and an eye refractive power measuring mode switch 80 and an opacity observation mode switch 81 are also connected to the data bus circuit 74 through an operation switch input circuit 82. Furthermore, an fixation target visibility adjustment circuit 83 for moving the lens 64, an MPU 84, a ROM 85 and a RAM 86 are connected to the data bus circuit 74.

The MPU 84, functioning according to a program stored in the ROM 85, controls the light source control circuit 79, the operation switch input circuit 82, the image symbol generation circuit 77, the fixation target visibility adjustment circuit 83. The RAM 86 is used as a memory in the processing and storage of the measured values in the MPU 84.

When the light sources 69a, 69b for illuminating the anterior segment of the eye are turned on by the light source control circuit 79, the image of the anterior segment of the eye is provided on the imaging device 68. The imaging device 68 is driven by the imaging device driving circuit 75. The image signal from the imaging device 68 is synthesized in the image signal synthesis circuit 76 with an alignment mark generated by the image symbol generation circuit 77, whereby the image of the anterior segment of the eye is displayed, together with the alignment mark, on the monitor 78. The examiner executes the alignment and focuses, while observing the monitor 78, in such a manner that the alignment mark becomes positioned at the center of the pupil Ep.

After the alignment, the measuring mode switch 80 is depressed, whereby the lens 64 is driven by the fixation target visibility adjustment circuit 82 through the data bus circuit 74 to vary the visibility of the target 65, thus accommodation of the eye to be examined E is relaxed.

When the measuring light source 52 is turned on, the reflected images Q1–Q6 are projected on the imaging device 61 as shown in FIG. 7. The images Q1–Q6 are stored, as digitized image signals, in the image memory 73 through the A/D converter 72, and the refractive power of the eye is calculated by the MPU 84, based on the image information thus stored in the image memory 73.

Figure 9:
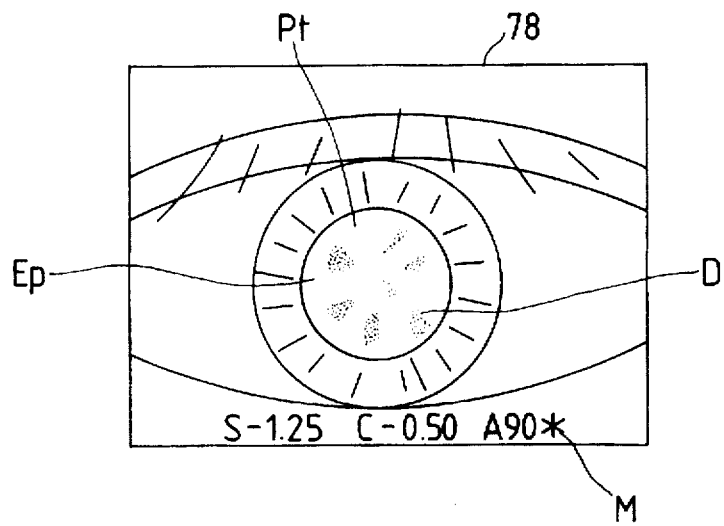
FIGS. 9 and 10 are schematic views of an image, displayed on a television monitor, in the cataract observation mode and in the continuous eye retractomery mode.

In case the measurement of the eye to be examined E is not possible for example due to opacity, the opacity observation mode switch 81 is depressed to adopt a mode for observing the opacity and for continuous measurement of the refractive power of the eye, whereupon the measuring light source 52 is continuously turned on to project the image by retroillumination on the imaging device 68 and to display the image Pt on the monitor 78 as shown in FIG. 9, wherein a opacity portion is represented by a shadow area D. If the reflected light beam from the ocular fundus Er can be received by the imaging device 61, the measured values are also displayed in the lower part of the display. If the reliability of the measured values is somewhat low, a mark M is displayed at the lower right part of the display.

The examiner executes alignment by moving the apparatus in the vertical and lateral directions, while observing the monitor 78, in such a manner that the measuring light beam aligns in a part outside the shadow D of the opacity. A position enabling proper measurement may be confirmed from the displayed values of measurement. After the position enabling proper measurement is confirmed, the refractive power measurement switch 80 is depressed, whereby the lens 64 is moved by the fixation target mark visibility adjustment circuit 82 to vary the visibility of the fixed target 65 accommodation of the eye to be examined is relaxed. Thus the refractive power of the eye is measured.

In the embodiment explained above, the cataract observation mode switch 81 is provided to shift the operation mode from the ordinary measuring mode, but the switch 81 may be dispensed with and the cataract observation mode may be always adopted for the measurement.

Figure 10:
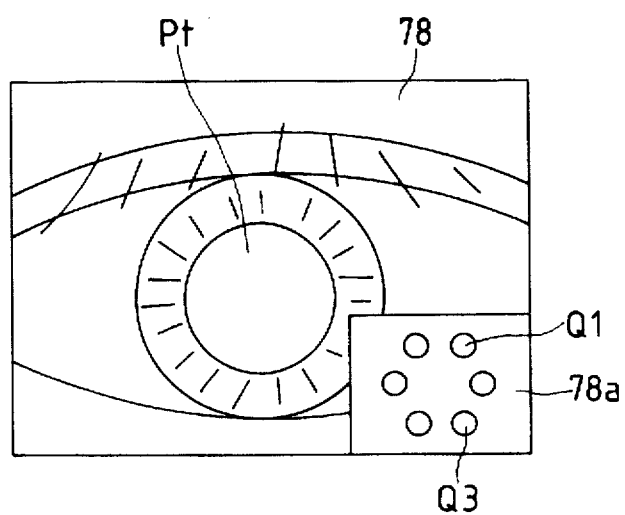

In the continuous eye refractive in the opacity observation mode, it is also possible to omit the display of the measured values on the monitor 78 but to only display the mark M, shown in FIG. 9, for indicating whether the measurement is possible. It is furthermore possible to directly display the reflected images Q1–Q6, projected on the imaging device 61, in a sub-image area 78a of the monitor 78 as shown in FIG. 10 and to effect the alignment in such a manner that the images become visible in optimum state.

Figure 11:
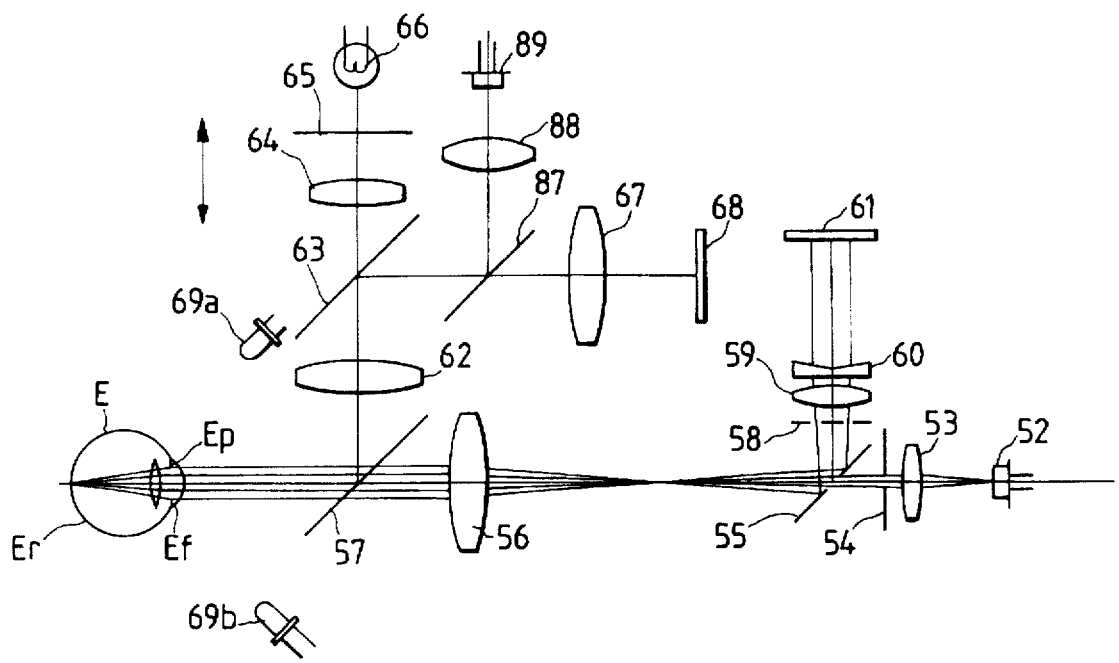
FIG. 11 is a schematic view of a third embodiment.

It is furthermore possible to illuminate the pupil area with a light source different from the measuring light source 52. FIG. 11 shows a third embodiment equipped with an exclusive light source, for illuminating the pupil area, of a wavelength different from that of the measuring light source 52, wherein equivalent components to those in FIG. 5 are represented by same numerals. The embodiment is different from that shown in FIG. 5, on the optical path in the direction of reflection of the dichroic mirror 63 there is provided a half mirror 87, and, on an optical path in the direction of reflection thereof, there are provided a lens 88 and a pupil illuminating light source 89.

The light beam from the pupil illuminating light source 89 is guided through the lens 88, then reflected by the half mirror 87 and is projected onto the ocular fundus Er. The reflected light beam therefrom is reflected by the dichroic mirror 57, then guided through the lens 62, and reflected by dichroic mirror 63 and transmitted by half mirror 87 and guided through lens 67 and projects, on the imaging device 68, an image Pt by retroillumination, which is displayed on the monitor 78.

This embodiment, though employing an additional light source, provides an advantage of improved efficiency of the light sources, since the wavelengths of the light sources can be almost completely separated by the dichroic mirrors 57, 63.

Figure 12:
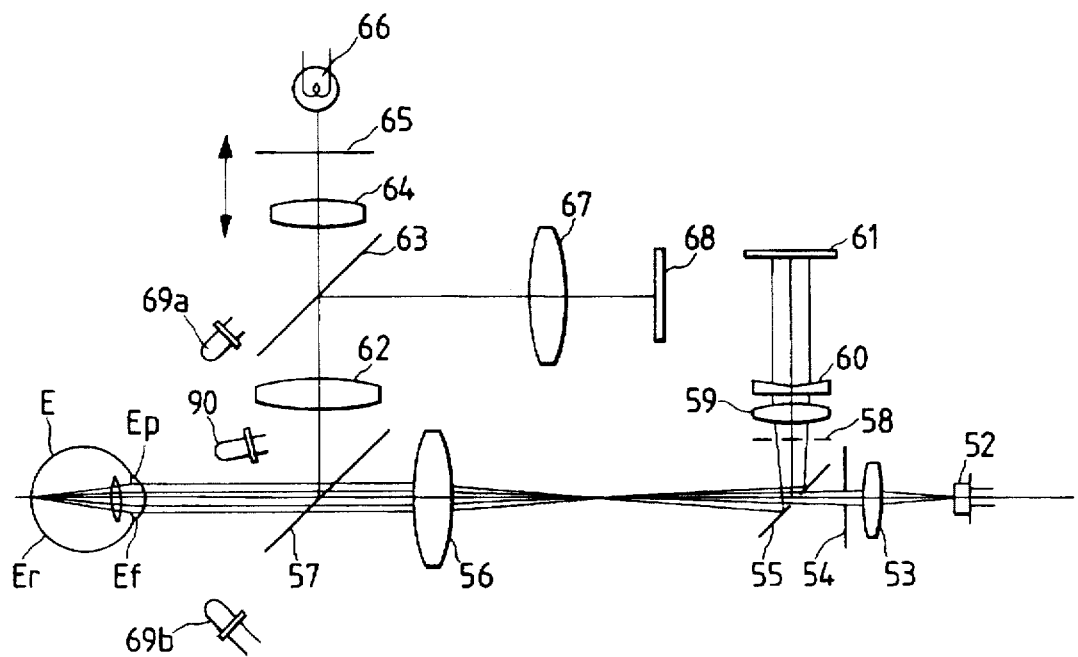
FIG. 12 is a schematic view of a fourth embodiment.

FIG. 12 shows a fourth embodiment for directly illuminating the pupil Ep from a position in front of the anterior part Ef of the eye, wherein equivalent components to those in FIG. 5 are represented by same numerals. It is different from the embodiment shown in FIG. 5, that a pupil illuminating light source 90 is provided in a position, in front of the anterior part Ef and capable of directly illuminating the pupil Ep.

The light beam from the light source 90 illuminates the pupil Ep, and the reflected light beam therefrom is reflected by the dichroic mirror 57, and guided through lens 62, and reflected by dichroic mirror 63 and guided through lens 67, and projects an image Pt on the imaging device 68. In this case different from the second, third and forth embodiments, the opacity of the eye is illuminated directly, so the image of the opacity can be shown more brightly. The light sources 69a, 69b may be used instead of the pupil illuminating light source 90 for illuminating the anterior segment of the eye.

Figures 13, 13A:
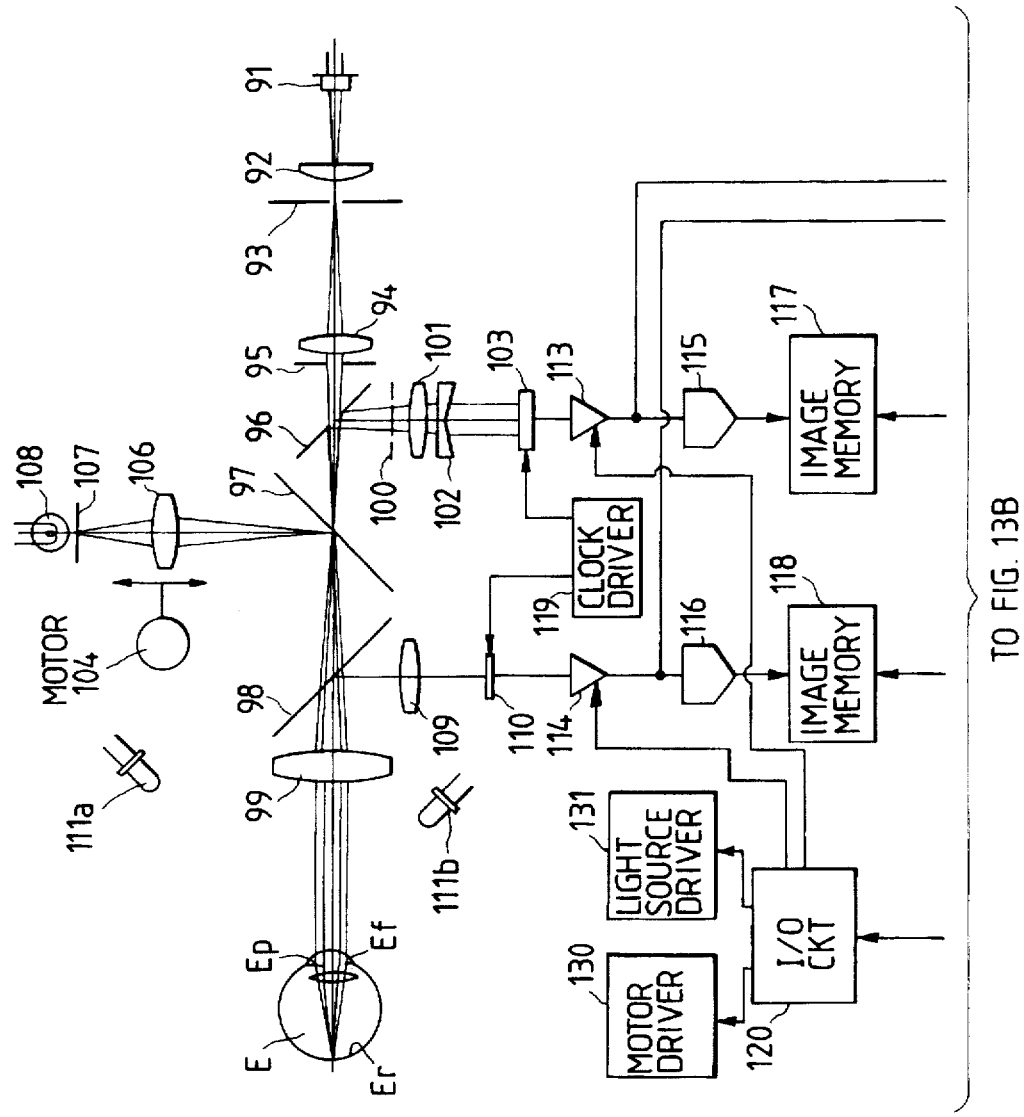
FIG. 13 is comprised of FIGS. 13A and 13B are schematic views of a fifth embodiment.
Figure 13B:
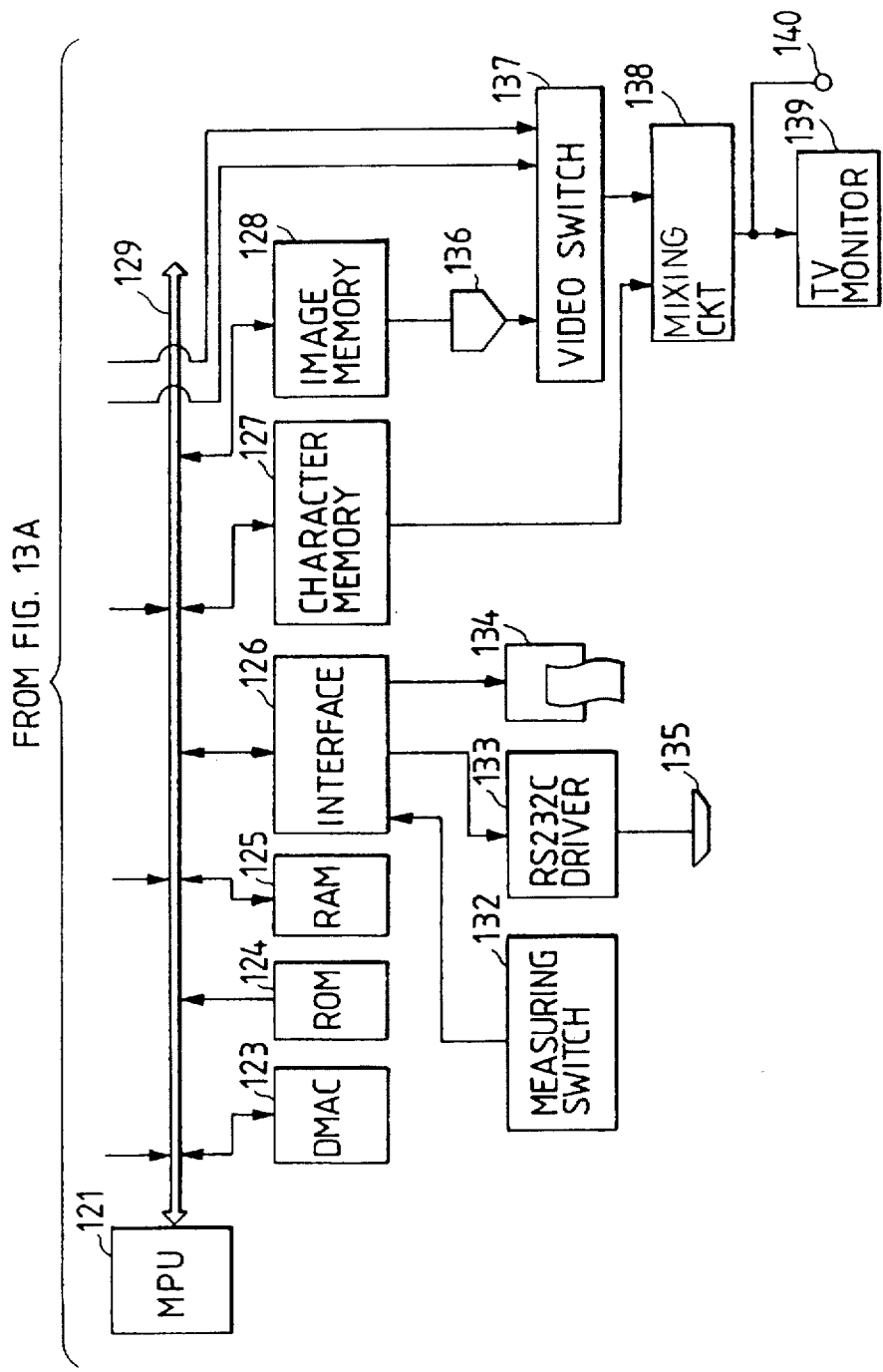

FIGS. 13A and 13B show the configuration of a fifth embodiment, wherein, on an optical path from an infrared measuring light source 91 to the eye to be examined E, there are provided a condenser lens 92, a measuring target 93, a relay lens 94, a center-aperture diaphragm 95, a holed mirror 96, light splitting mirrors 97, 98 and an objective lens 99. On an optical path in the direction of reflection of the hole mirror 96, there are provided a multi-aperture diaphragm 100 having six apertures as shown in FIG. 2, a relay lens 101, a splitting prism 102 consisting of six prisms, and a video image detecter device 103.

Also on an optical path in the direction of reflection of the light splitting mirror 97 there are provided a relay lens 106 axially movable by a motor 104, a fixation target 107, and a light source 108 for illuminating the fixation target 107. On an optical path in the direction of reflection of the light splitting mirror 98 there are provided a relay lens 109 and an imaging device 110. Diagonally in front of the anterior segment of the eye Ef there are provided light sources 111a, 111b for illuminating the anterior segment of the eye. The center-aperture diaphragm 95 and the multi-aperture diaphragm 100 are optically conjugate with the pupil Ep. The light splitting mirror 98 has spectral characteristics of reflecting and transmitting the infrared light with certain proportions and transmitting the visible light, while the light splitting mirror 98 has spectral characteristics of transmitting the infrared light and reflecting the visible light.

The outputs of the video image detector 103, 110 are supplied, respectively in succession, to signal processing amplifiers 113, 114, A/D converters 115, 116, and image memories 117, 118, and a clock driver 119 supplies the imaging devices 103, 110 with synchronizing clock signals. Also an I/O circuit 120, an MPU 121, a direct memory access control circuit (DMAC) 123, a ROM 124, a RAM 125, an interface 126, a character memory 127, and an image memory 128 are connected to a data bus circuit 129, together with the image memories 117, 118.

The output of the I/O circuit 120 is connected to a motor driver 130 for controlling the motor 104, a light source driver 131 for controlling the light sources such as the measuring light source 91, and the signal processing amplifiers 113, 114. The input terminal of the interface 126 is connected to a measuring switch 132, and the output terminal is connected to an RS232C driver 133 for releasing the results of measurements and the information stored in the image memories 117, 118, and also to a printer 134 for printing the results of measurements, and the output of the RS232C driver 133 is supplied to the exterior through an RS232C output terminal 135.

Also the output of the image memory 128 is connected to a D/A converter 136 and a video switch 137, which also receives the outputs of the signal processing amplifiers 113, 114 and of which input signals are switched by the MPU 121. The output of the video switch 137 is supplied, together with the output of the character memory 127, to a mixing circuit 138, of which output is connected to a display monitor 139 and an external output terminal 140.

The light sources 111a, 111b widely illuminate the anterior part Ef of the eye, and the reflected light beam therefrom is guided through the objective lens 99, light splitting mirror 98 and relay lens 109 and is focused as an image of the anterior part of the eye on the imaging device 110. The output signal therefrom is converted into a video signal by the signal processing amplifier 114, then digitized by the A/D converter 116 and stored in the image memory 118. The video signal from the amplifier 114 is simultaneously supplied also to the video switch 137.

Figure 14:
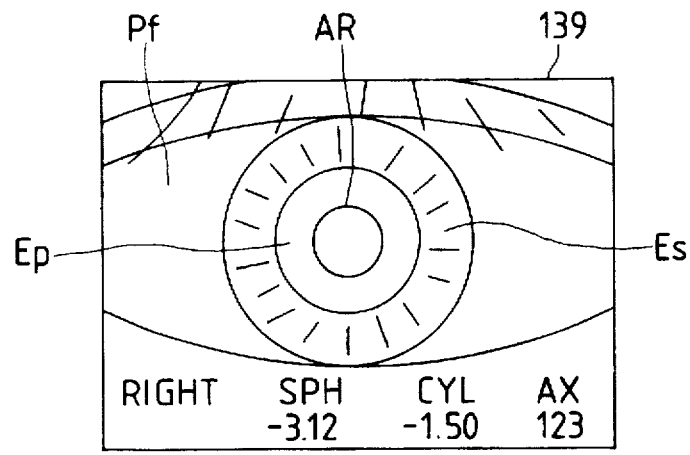
FIG. 14 is a schematic view of an image of the anterior segment of the eye, displayed on a television monitor.

The character memory 127 stores data for displaying the results of measurements and the alignment mark on the monitor 139, and the output of the memory 127 is mixed, in the mixing circuit 138, with the video signal from the video switch 137, whereby an alignment ring AR is displayed on the display monitor 139 as shown in FIG. 14, together with the image Pf of the anterior segment of the eye including the pupil Ep and the iris Es, and the examiner executes alignment of the eye to be examined E and the apparatus, while observing the display monitor 139.

The light beam from the light source 108 illuminates the fixation target 107, then is guided through the relay lens 109, light splitting mirrors 97, 98 and objective lens 99 and is projected onto the ocular fundus Er. The motor 21 axially moves the relay lens 109 according to the output of the motor driver 130, thereby fogging the fixation target 107 according to the refractive power of the eye to be examined E, and fixing the line of sight of the eye to be examined.

Figure 15:
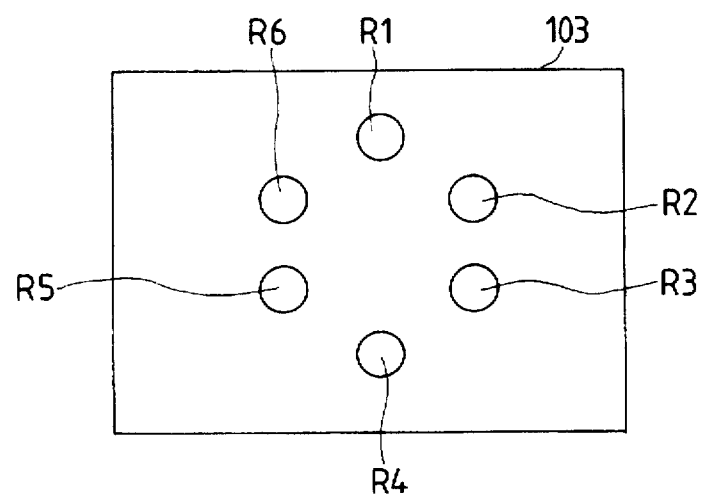
FIG. 15 is a schematic view of an image, formed by the light reflected at the ocular fundus and received by the imaging device.

The light beam from the measuring light source 91 illuminates the measuring target 93 through the condenser lens 92, then is guided through the relay lens 94, center-aperture diaphragm 95, holed mirror 96, light splitting mirrors 97, 98 and objective lens 99 and projected onto the ocular fundus Er. The reflected light beam therefrom is guided through the objective lens 99 and is partly transmitted and reflected by the splitting mirror 98. The transmitted light beam is guided through the light splitting mirror 97, holed mirror 96, multi-aperture diaphragm 100 and relay lens 101, then split and deflected by the splitting prism 102 and is focused as the reflected images R1-R6 as shown in FIG. 15 on the imaging device 103.

The output signal from the imaging device 103 is converted into a video signal by the signal processing amplifier 113, then digitized by the A/D converter 115 and stored in the image memory 117. Then the image stored in the image memory 117 is checked, and, if it is normal, the refractive power is calculated, based on the coordinates of centers of gravity of the small circles constituting the images R1-R6. The video signal from the amplifier 113 is also supplied to the video switch 137.

Figure 16:
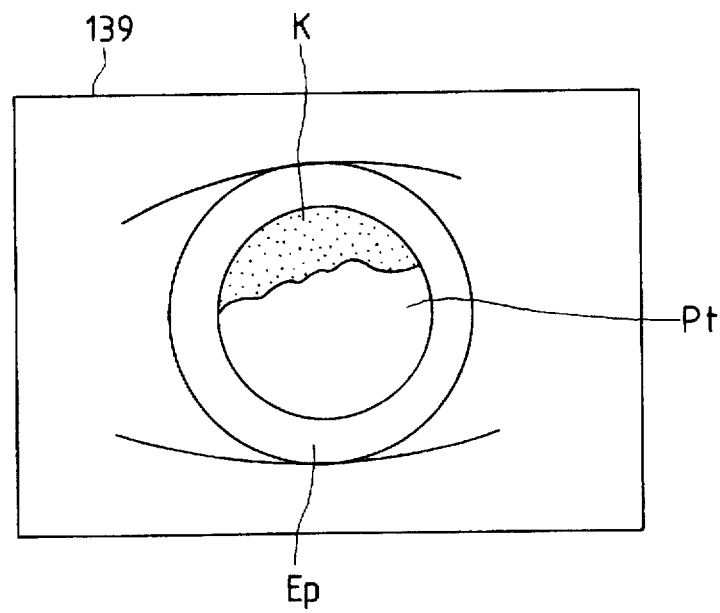
FIG. 16 is a schematic view of an image formed by retroillumination, displayed on the television monitor.

On the other hand, the light beam reflected by the splitting mirror 98 is guided through the relay lens 109 and focused as an image by retroillumination on video image detector 110. The output signal therefrom is converted into a video signal by the signal processing amplifier 114, then digitized in the A/D converter 116 and stored in the image memory 118. The video signal from the amplifier 114 is supplied also to the video switch 137, and is displayed, through the mixing circuit 138, as the image Pt by retroillumination on the display monitor 139 as shown in FIG. 16. The light sources 111a, 111b for illuminating the anterior segment of the eye are turned off at the observation of the image Pt by retroillumination. Consequently the pupil Ep of the image Pt appears generally brighter, whereas the surrounding area appears darker. A cataract portion K appears darker like a shadow. If the cataract is present over the entire pupil Ep, it appears generally bright since the opacity portion is directly illuminated by the measuring light source 91.

In the actual eye refractometry, the light sources 111a, 111b for illuminating the anterior segment of the eye are turned on, and the examiner executes the alignment with the eye to be examined E, by observing the monitor 139. More specifically, the examiner adjusts the apparatus in the vertical and lateral directions and working distance, by means of an unshown operating joystick, in such a manner that the alignment ring AR and the pupil Ep become substantially concentric, as shown in FIG. 14. After the alignment, the measuring switch 132 is pressed, whereby the light sources 111a, 111b are turned off while the light source 108 for illuminating the target is turned on, thereby fixing the line of sight of the eye to be examined E. Then the measuring light source 91 is turned on to form the images R1-R6, by the reflection at the ocular fundus Er, on video image detector 103, and to store the corresponding image signal in the image memory 117. At the same time the image Pt by retroillumination of the pupil area is projected on video image detector 110, and the image signal thereof is stored in the image memory 118.

Then the light sources 111a, 111b for illuminating the anterior segment of the eye are turned on again, then the MPU 121 checks whether the image information in the image memory 117 is normal by the program stored in the ROM 124, and, if normal, the refractive power of the eye is calculated from the image information. The calculated result is also checked, and, if it is normal, the calculated refractive power of the eye is converted into the next data, stored to the character memory 127, and displayed through the mixed circuit 138 in the lower part of the display monitor 139 as shown in FIG. 14. At the left-hand part there is displayed that the eye to be examined is the right side eye.

Figure 17:
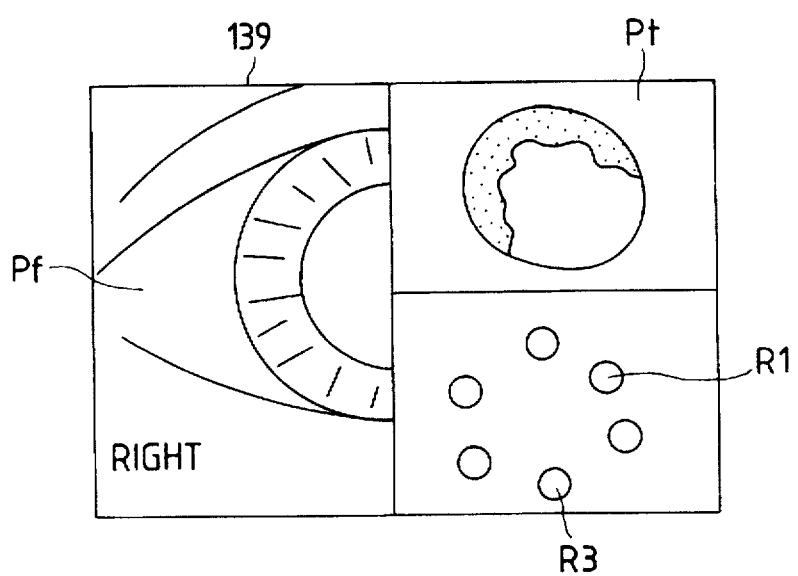
FIG. 17 is a schematic view of an image of the anterior segment of the eye and an image formed by retroillumination and an image formed by the light reflected from the ocular fundus, both reduced in size to ¼, displayed on the television monitor.

If the image information or the result of calculation in the image memory 117 is abnormal, an error message is displayed on the monitor 139, and an error flag in the RAM 125 is set at "1", indicating the error in the first time. Then the measuring switch 132 is pressed again to effect the image processing in the same manner, and the error flag is increased every time the error is displayed. When the error flag reaches a predetermined value, the image in the image memories 118, 117 are transferred to the image memory 128 with such compression as to reduce the image size to ¼ on the display monitor 139, and further supplied to the video switch 137 through the D/A converter 137, whereby the display monitor 139 displays the image Pt by retroillumination of the pupil and the images R1-R6, both reduced in size to ¼, together with the image Rf of the anterior segment as shown in FIG. 17, and the error flag is reset.

The image data of the image memory 117 are transferred, by every other pixel in the horizontal and vertical directions, by the DMAC 123 to the image memory 128, and the video switch 137 is appropriately controlled, whereby the results of measurements and the marks entered into the character memory 128 and thus transferred image information are displayed, together with the image of the anterior segment of the eye Pf, on the display monitor 139. The DMAC 123 is provided for high-speed data transfer from the image information in the image memories 117, 118 directly to the RAM 125 or the image memory 128, without entering through the MPU 121.

Figures 18, 18A:
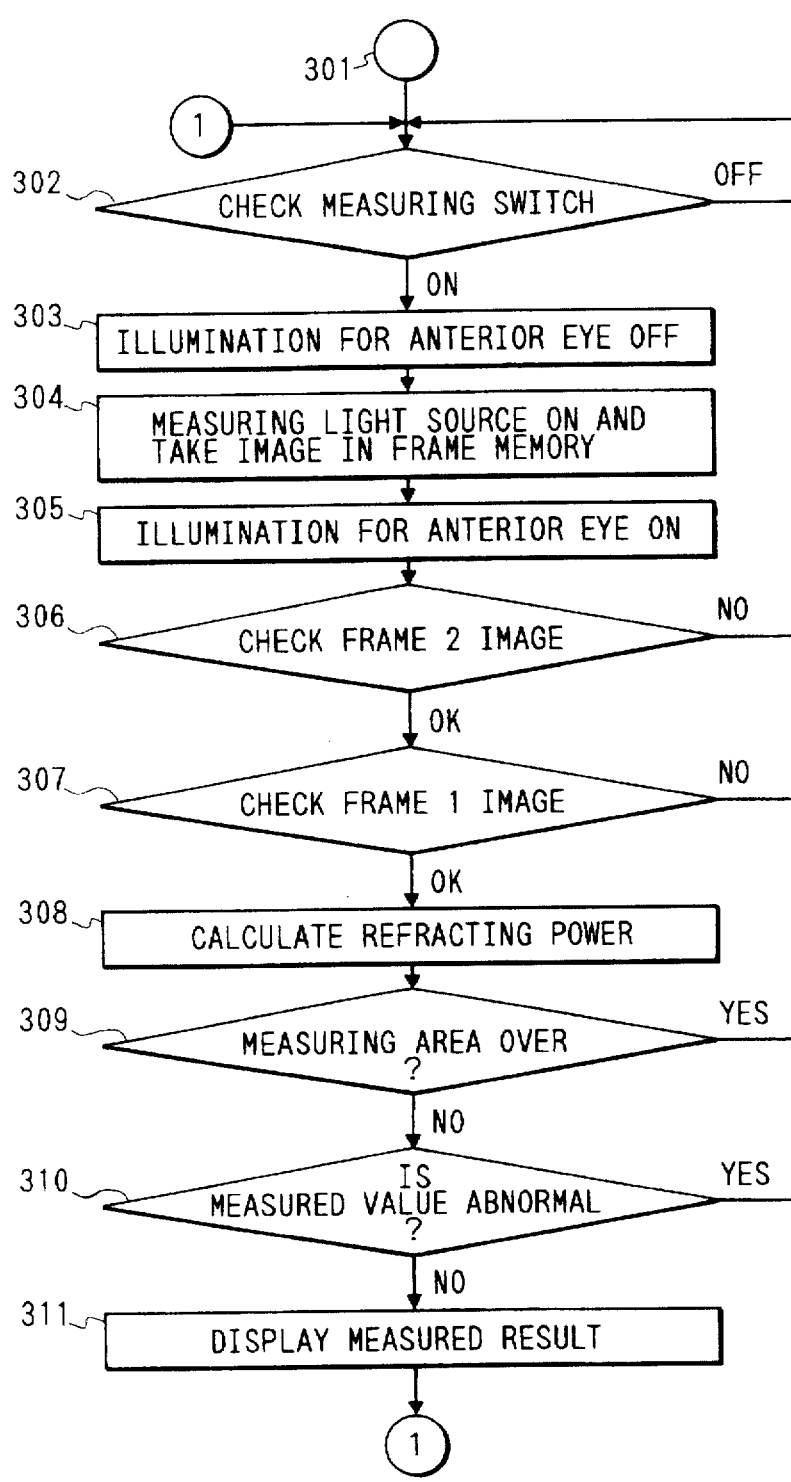
FIG. 18 is comprised of FIGS. 18A and 18B are flow charts of the control sequence of measurement process means.
Figure 18B:
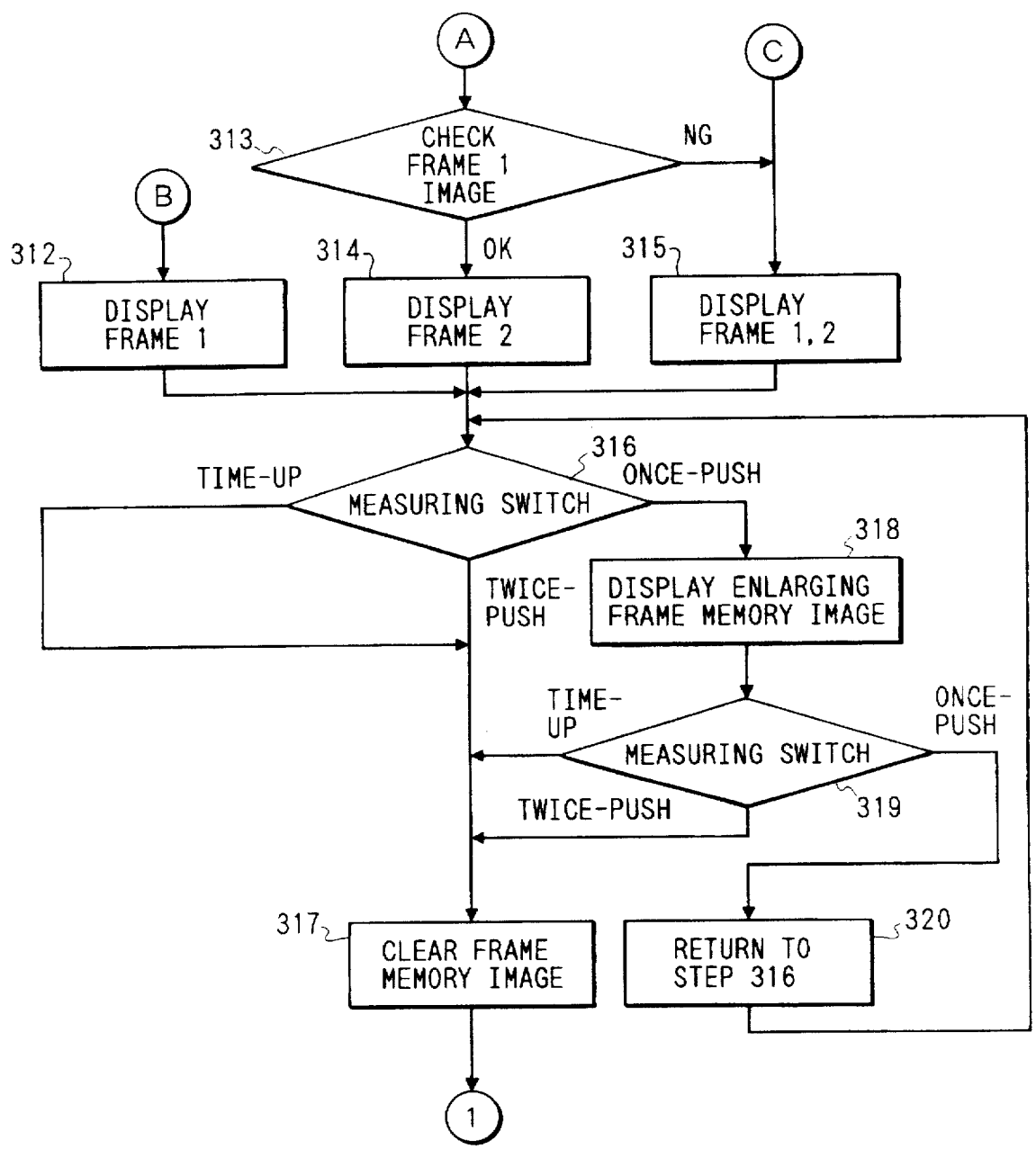

FIGS. 18A and 18B are flow charts showing the control sequence for the measurement in this case. At a step 301 the light sources 111a, 111b are turned on for alignment. If at a step 302 identifies the state that measuring switch 132 is pressed is detected, the sequence proceeds to a step 303 and if not, the sequence returns to the step 301. At the step 303 the light sources 111a, 111b are turned off. Then at a step 304 the measuring light source 91 are turned on, and the images R1–R6 on video image detector 103 and the image Pt by retroillumination on video image detector 110 are stored in the image memories 117, 118. At a step 305 the light sources 111a, 111b are turned on again.

At a step 306 it is checked whether the number of spots constituting the images R1–R6 stored in the image memory 117, the light quantities, areas, shapes and balance thereof are normal, and, if they are normal or abnormal, the sequence respectively proceeds to a step 307 or 313. At the step 307 the shape, luminance and number of bright areas of the image Pt of the retroillumination image stored in the image memory 118, are checked and, if the result is normal or abnormal, the sequence respectively proceeds to a step 308 or 312. At the step 308 the refractive power of the eye is calculated from the image information in the image memory 118.

At next step 309 it is checked whether the result of the calculation is within the range of measurement, and, if within or otherwise, the sequence proceeds respectively to a step 310 or 315. At the step 310 it is checked whether the result indicates an abnormal result, such as the cylinder power equal to or larger than +5D or sphere power equal at least to +5D or −10D, and, if not, the sequence proceeds to a step 311 for storing the result of measurement in the character memory 127 and displaying it on the display monitor 139. Then the sequence returns to the step 302. On the other hand, if the result is identified abnormal, the sequence proceeds to a step 315.

Figure 19:
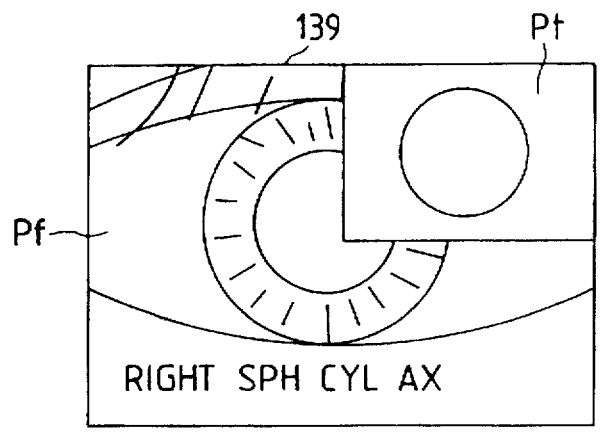
FIG. 19 is a schematic view of an image of the anterior segment of the eye, and an image formed by retroillumination and reduced in size to ¼, displayed on the television monitor.
Figure 20:
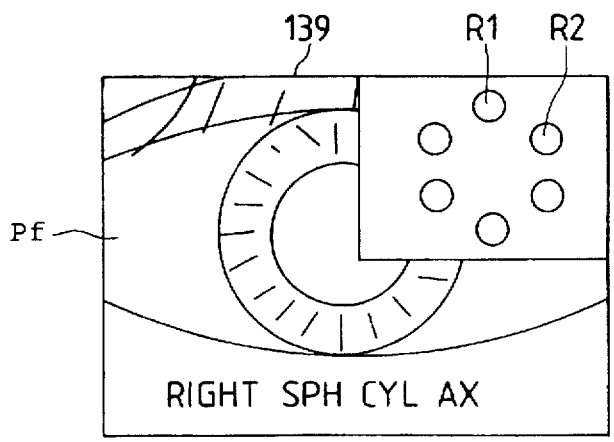
FIG. 20 is a schematic view of an image of the anterior segment of the eye, and an image formed by the light reflected at the ocular fundus and reduced in size to ¼, displayed on the television monitor.

If the image information in the image memory 117 is abnormal, at the step 312 the image Pt by retroillumination is sent from the image memory 117 to 128 with compression, thereby displaying the image, compressed to ¼, together with the image of the anterior segment Pf as shown in FIG. 19 on the monitor 139, and the sequence proceeds to a step 316. Also if the abnormality is found in the step 306, at the step 313 it is checked whether the image information in the image memory 118 is normal, and, if normal or otherwise, the sequence proceeds respectively to a step 314 or 315. At the step 314 the images R1–R6 with compression is sent from the image memory 118 to 128, thereby displaying the images R1–R6 reduced in size to ¼, together with the image of the anterior segment Pf on the display monitor 139 as shown in FIG. 20, and then the sequence proceeds to a step 316.

In case at the step 314 abnormality is found, or at the step 309 it is identified that the range of measurement is excessive, or the step 310 finds an abnormal result of measurement, at the step 315 the image Pt by retroillumination and the images R1–R6 are transfered from the image memories 117, 118 to 128 with a size compression to ¼ on the display monitor 139, thereby displaying the images together with the image of the anterior segment Pf as shown in FIG. 17, and the sequence then proceeds to a step 316. At the step 316 the state that the measuring switch 132 is pressed is waited and, if the switch 132 is pressed twice without interruption or if a predetermined time elapses, at a step 317 the images are erased in the image memories 117, 118 and the image Pf of the anterior image is displayed only on the display monitor 139 as shown in FIG. 14. Then the sequence returns to the step 302.

If the switch 132 is pressed once, at a step 318 the compressed images from the image memories 117, 118 are displayed on the display monitor 139 with enlargement to the full image field thereof, for observation of the image Pt by retroillumination and the images R1–R6. A next step 319 again awaits the state that the measuring switch 132 is pressed is waited, and, in response to a switch-press, at a step 320 the display is returned to the original state shown in FIG. 17 and the sequence proceeds to the step 316. If the switch is actuated twice without interruption or a predetermined time elapses, the sequence proceeds to a step 317.

In the course of above-explained process, in response to a number of error equal to the predetermined number and after the images in the image memories 117, 118 are displayed in reduced manner in size to ¼ as shown in FIG. 17, the display on the display monitor 139 may be switched according to the actuation of the measuring switch 132 as in the sequence starting from the step 316 in FIG. 18B. It is also possible to record the fluctuation in the measured values, and, if the fluctuation is large, to display the images R1–R6 and the image Pt by retroillumination, stored in the image memories 117, 118, in reduced mode in size to ¼, as shown in FIG. 17.

Figure 21:
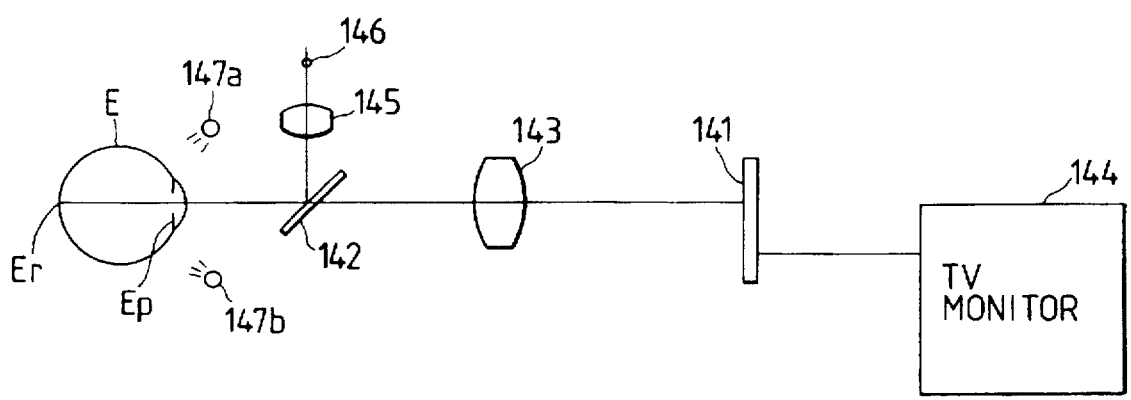
FIG. 21 is a schematic view of a sixth embodiment.

FIG. 21 is a schematic view of a sixth embodiment, wherein, on an optical path from the eye to be examined E to an imaging device 141, there are provided a light splitting member 142 and a lens 143, and the output of the imaging device 141 is connected to a television monitor 144. The pupil Ep of the eye to be examined is substantially conjugate with the imaging device 141, with respect to the lens 143. Also on an optical path in the direction of reflection of the light splitting member 142, there are provided a lens 145 and a near infrared light source 146, and, diagonally in front of the anterior segment Ef of the eye, there are provided light sources 147a, 147b for illuminating the anterior segment.

Figure 22:
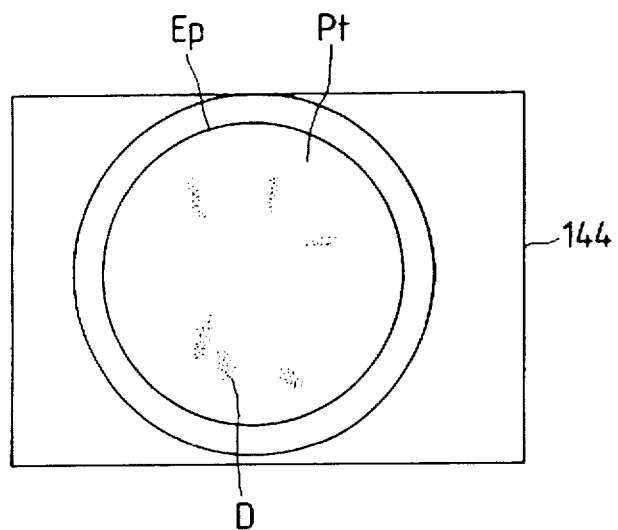
FIG. 22 is a schematic view of an image formed by retroillumination and displayed on the television monitor.

The light beam from the near-infrared light source 146 is guided through the lens 145, then reflected by the splitting member 142 and is projected onto the ocular fundus Er of the eye to be examined E. The reflected light beam therefrom illuminates the pupil Ep, then guided through the splitting member 142 and lens 143, focused on the imaging device 141 as an image Pt by retroillumination and is displayed on a monitor 144 as shown in FIG. 22.

Figure 23:
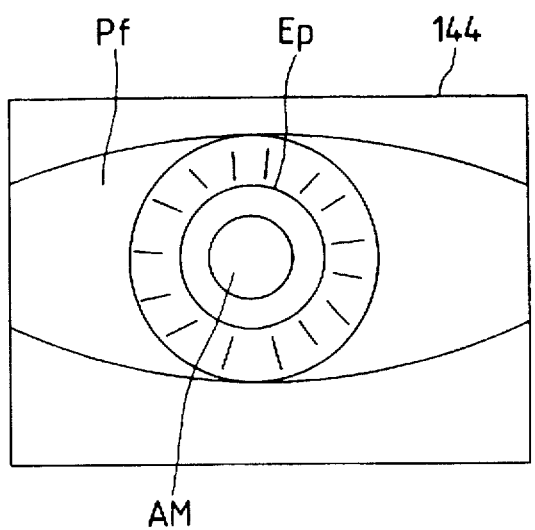
FIG. 23 is a schematic view of an image of the anterior segment of the eye, displayed on the television monitor.

The light beams from the light sources 147a, 147b illuminate the anterior segment Ef of the eye, and then guided through the splitting member 142 and lens 143, focused on the imaging device 141 as an image Pf of the anterior segment of the eye, and displayed on the monitor 144 as shown in FIG. 23.

When the examiner actuates an unshown power switch or an unshown anterior segment alignment switch, the near-infrared light source 146 is turned off while the light sources 147a, 147b for illuminating the anterior segment are turned on, whereby the monitor 144 displays, as shown in FIG. 23, the image Pf of the anterior segment of the eye together with an annular alignment mark AM. The examiner executes the alignment in the vertical and lateral directions, while observing the monitor 144, in such a manner that the pupil Ep and the alignment mark AM become substantially concentric, and also executes the alignment in the axial direction of the eye to be examined E, observing the sharpness of the image Pf of the anterior segment of the eye.

Then, when an unshown retroillumination observation switch is actuated, the near-infrared light source 146 is turned on while the light sources 147a, 147b are turned off, but these light sources may remain turned on. The monitor 144 displays the image Pt by retroillumination, magnified by the known electric zoom method, as shown in FIG. 22, and a opacity portion D eventually present in the eye to be examined E can be observed as a shadow.

If the opacity portion D of the image Pt by retroillumination is not sharp, the apparatus can be focused to the opacity portion D by an axial movement.

And further in this embodiment, the magnification of observation is fixed, but there may be provided a switch for varying the magnification. And further two polarizing plates with mutually orthogonal polarizing axes may be respectively provided on the two optical paths, in order to intercept the light beam reflected by the cornea.

Figure 24:
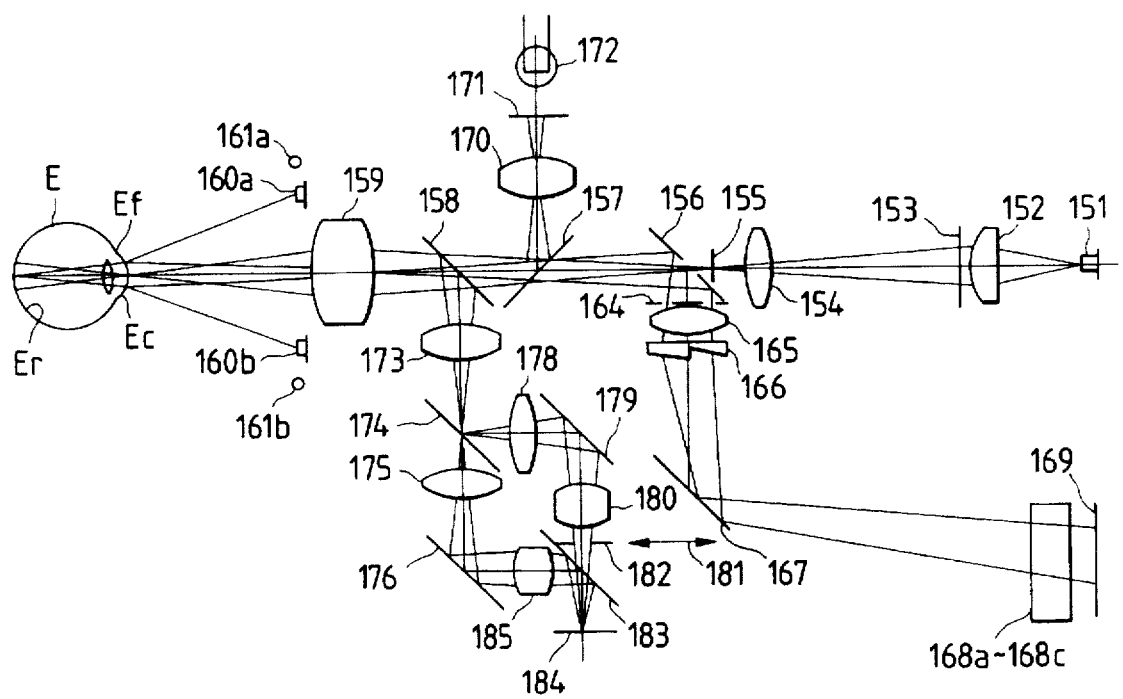
FIG. 24 is a schematic view of a seventh embodiment.
Figure 25:
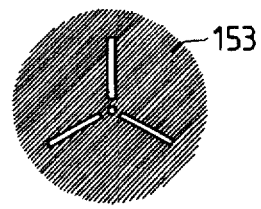
FIG. 25 is an elevation view of an index mark for eye refractometry.
Figure 26:
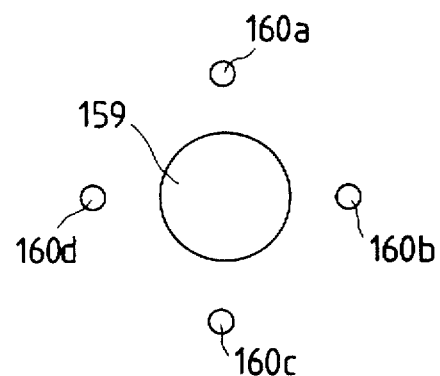
FIG. 26 is a schematic view explaining the positional relationship between the objective lens and an index mark for measuring the shape of cornea.

FIG. 24 schematically shows a seventh embodiment provided with functions of measuring the refractive power of the eye and the shape of cornea, wherein, on an optical path from a light source 151 for eye refractometry to the eye to be examined E, there are provided a condenser lens 152, a target 153 for eye refractometry as shown in FIG. 25, a relay lens 154, a aperture 155, a holed mirror 156, light splitting mirrors 157, 158, and an objective lens 159. Around the objective lens 159 and diagonally in front of the eye to be examined E, there are provided four targets 160a–160d as shown in FIG. 26, for measuring the cornea shape. Also diagonally in front of the eye to be examined E there are provided light sources 161a, 161b for illuminating the anterior segment of the eye.

Figure 27:
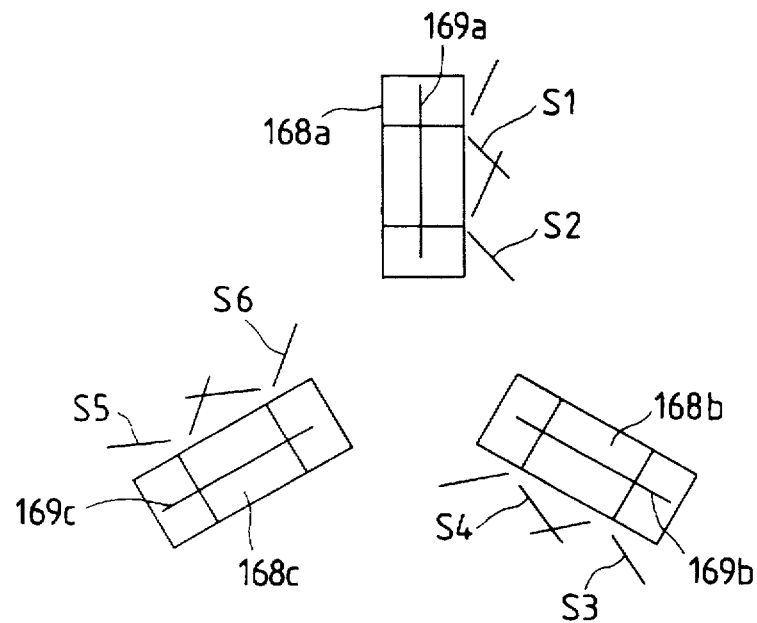
FIG. 27 is a schematic view showing images formed by reflected light.

On an optical path in the direction of reflection of the holed mirror 156 there are provided a multi-aperture diaphragm 164 having six apertures as in FIG. 2, a relay lens 165, a splitting prism 166 consisting of fix prisms, a mirror 167, cylindrical lenses 168a–168c and a position detector 169 consisting of three one-dimensional position detecting elements 169a–169c such as CCD's, thus constituting an optical system for eye refractometry. The cylindrical lenses 168a–168c and the position detecting elements 169a–169c are positioned as shown in FIG. 27, when seen axially. More specifically, the cylindrical lenses 168a–168c have refractive powers in directions orthogonal to the detecting directions of the elements 169a–169c, and serve to concentrate the light beams in the directions onto the position detecting elements 169a–169c.

Also on an optical path in the direction of reflection of the light splitting mirror 157, there are provided a relay lens 170, a fixation target 171, and a light source 172 for illuminating the target, and, on an optical path in the direction of reflection of the light splitting mirror 158 there are provided a relay lens 173, a light splitting mirror 174, a field lens 175, and a mirror 176. Further, on an optical path in the direction of reflection of the light splitting mirror 174, there are provided a field lens 178, a mirror 179, a field lens 180, an aperture 182 retractable from the optical path by driving means 181, a dichroic mirror 183 and an imaging device 184, thereby constituting an optical system for measuring the cornea shape, and, on an optical path in the direction of reflection of the mirror 176, leading to the dichroic mirror 183, there is provided a lens 185, thereby contsituting an optical system for observing the anterior segment of the eye.

The aperture 182 is moved by the driving means 181 to a position where the magnification of the targets 160a–160d for measuring the cornea shape remains constant regardless of the operating distance between the apparatus and the eye to be examined E, namely a position where the principal ray of the corneal reflected image, which is a false image of the targets 160a–160d in the eye to be examined E at the appropriate and inappropriate operating distances crosses the optical axis after passing the optical system explained above.

In the eye refractometry, the light beam from the light source 151 illuminates the target 153 for eye refractometry after passing the condenser lens 152, then is guided through the relay lens 154, aperture 155, holed mirror 156, light splitting mirrors 157, 158 and objective lens 159 and is projected onto the ocular fundus Er of the eye to be examined E. The reflected light beam therefrom is guided through the objective lens 159, light splitting mirrors 158, 157, holed mirror 156, apertures of the multi-aperture diaphragm 164 and a relay lens 165 and is split and deflected by the splitting prism 166. It is then guided through the mirror 167 and the cylindrical lenses 168a–168c and projected as six reflected images S1–S6 on the position detecting elements 169a–169c as shown in FIG. 27.

The six reflected images S1–S6 mutually are overlapped on the optical axis if the ocular fundus Er and the position detector 169 are mutually conjugate, but are mutually separated by the splitting prism 166, so that the refractive power of the eye can be determined from the distances between the images S1 and S2, between those S3 and S4 and between those S5 and S6 focused on the elements 169a–169c.

Figure 28:
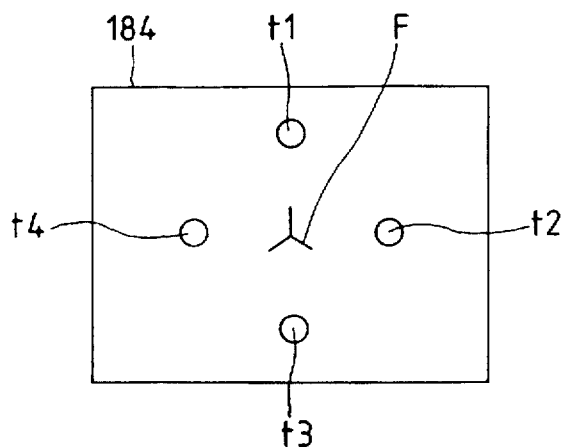
FIG. 28 is a schematic view of cornea-reflected light beams focused on the imaging device.

In the measurement of cornea shape, the light beams from the cornea shape measuring targets 160a–160d illuminate the cornea Ec, and the reflected light beam therefrom is guided through the objective lens 159, then focused through the light splitting mirror 158 and relay lens 173, and re-focused through the light splitting mirror 174, field lens 178, mirror 179, relay lens 180, aperture 182 and synthesizing mirror 183 as images t1–t4 on the imaging device as shown in FIG. 28.

The light beam from the light source 151 for eye refractometry is guided through the condenser lens 152, target 153 for eye refractometry, relay lens 154 aperture 155, aperture of the holed mirror 156, light splitting mirrors 157, 158 and objective lens 159 and illuminates the cornea Ec, and the reflected light beam therefrom is guided through the objective lens 159, light splitting mirror 158, relay lens 173, light splitting mirror 174, field lens 178, mirror 179, relay lens 180, aperture 182 and synthesizing mirror 183 and forms an image F on the imaging device 184 as shown in FIG. 28.

Since the light beam from the target 153 for eye refractometry is constantly emitted axially, the image F is considered at the geometrical center of the images t1–t4, if the targets 160a–160d for cornea shape measurement are positioned symmetrically around the optical axis. Since the cornea is generally considered as a toric surface, the images t1–t4 on the imaging device 184 are arranged on an oval having the center at the image F. Since the oval can be determined by three points with respect to the center, the shape of the cornea Ec can be obtained by determining the coordinates of arbitrary three of the images t1–t4, with the original point placed at the center of the image F, and calculating the shape of the oval.

It is also possible to detect the abnormal astigmatism, by comparing the distances to the images t1–t4 from the original point at the center of the image F. For example it is possible to compare an oval determined from the coordinates of the images t1, t2, t3 with an oval determined from the images t2, t3, t4, and, if their shapes are not much different, to display the average values of the ovals, but, if they are significantly different, to display an abnormal astigmatism mark indicating that the cornea Ec is aberrated from the toric surface. Also, even if the image t1 for example cannot be detected due to the positioning of the eyelid on the eye to be examined E, the shape of the cornea Ec can still be determined from the remaining images t2–t4.

Furthermore, even if the targets 160a–160d are not positioned symmetrically around the optical axis, a similar effect can still be obtained by positioning the images t1–t4 for example on a spherical surface of a known curvature.

For fixing the line of sight of the eye to be examined E during the measurement of the cornea shape or the refractive power, the light beam from the light source 172 illuminates the fixation target 171, then is guided through the relay lens 170, light splitting mirrors 157, 158 and objective lens 159 and is projected onto the ocular fundus Er. The examiner fixes the line of sight of the eye to be examined E by varying the apparent visibility, by moving the target 171.

The light beams from the light sources 161a, 161b illuminate the anterior segment of the eye Ef, and the reflected light beam therefrom is guided through the objective lens 159, light splitting mirror 158, relay lens 173, light splitting mirror 174, field lens 175, mirror 176, relay lens 185 and light splitting mirror 183 and is focused as an image Pf of the anterior segment of the eye on the imaging device 184 and displayed on an unshown monitor. The examiner effects alignment while observing the monitor.

Then a retroillumination observation switch is actuated to turn on the light source 151 for eye refractometry and to turn off the light sources 161a, 161b for illuminating the anterior segment of the eye, but the light sources may remain turned on. The aperture 182 is retracted by the driving means 181 from the optical path, whereby the light beam from the light source 151 is guided through the condenser lens 152, target 153 for eye refractometry, relay lens 154, aperture 155, aperture of the holed mirror 156, light splitting mirrors 157, 158 and objective lens 159 and illuminates the cornea Ec, and the reflected light beam therefrom is transmitted by the objective lens 159, then reflected by the light splitting mirror 158, then guided through the relay lens 173, light splitting mirror 174, field lens 178, mirror 179, field lens 180, and synthesizing mirror 183 and projected as an image by retroillumination on the imaging device 184, so that the image by retroillumination can be observed on the unshown monitor.

In this embodiment, the imaging magnification is selected larger in the cornea shape measuring optical system than in the anterior segment of the eye observing optical system, so that the image by retroillumination can be observed in magnified manner as in FIG. 22.

Figure 29:
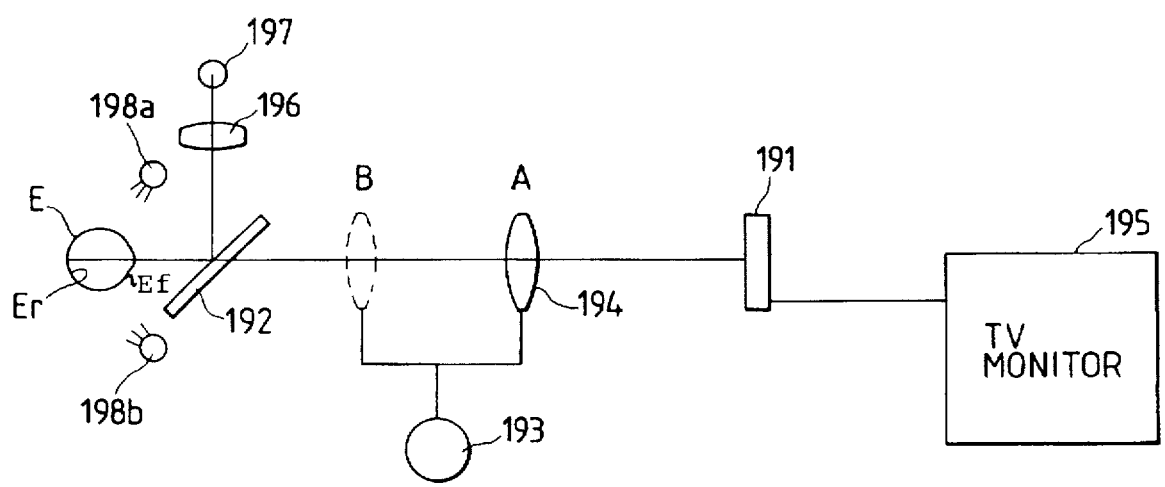
FIG. 29 is a schematic view of an eighth embodiment.

FIG. 29 is a schematic view of an eighth embodiment, wherein, on an optical path from the eye to be examined E to an imaging device 191 there are provided a light splitting member 192, and a movable lens 194 driven by lens driving means 193, and the output of the imaging device 191 is supplied to a television monitor 195. On an optical path in the direction of reflection of the light splitting member 192 there are provided a lens 196 and a near-infrared light source 197, and, diagonally in front of the anterior segment of the eye Ef, there are provided light sources 198a, 198b for illuminating the anterior segment.

The light beam from the light source 197 is guided through the lens 196, then reflected by the light splitting member 192 and projected onto the ocular fundus Er. The reflected light beam therefrom illuminates the pupil Ep, then is guided through the light splitting member 192 and the lens 194, then focused as an image Pt by retroillumination on the imaging device 191, and is displayed on the monitor 195.

At the observation of the anterior segment of the eye Ef, the light beams from the light sources 198a, 198b illuminate the anterior segment of the eye Ef, and the reflected light beam therefrom is guided through the light splitting member 192 and lens 194, then focused as an image of the anterior segment of the eye on the imaging device 191 and displayed on the monitor 195. Since the image on the device 191 is represented in size in inverted proportion to the object-image distance, the imaging magnification becomes larger when the movable lens 194 is in a position A than in a broken-lined position B. Thus the alignment of the anterior segment of the eye and the observation by retroillumination are preferably executed, with respective positioning of the movable lens 194 at the positions A and B. The imaging magnification of the observing system may be varied by a known zooming lens, thereby rendering the observing range of the image by retroillumination variable.

Figure 30:
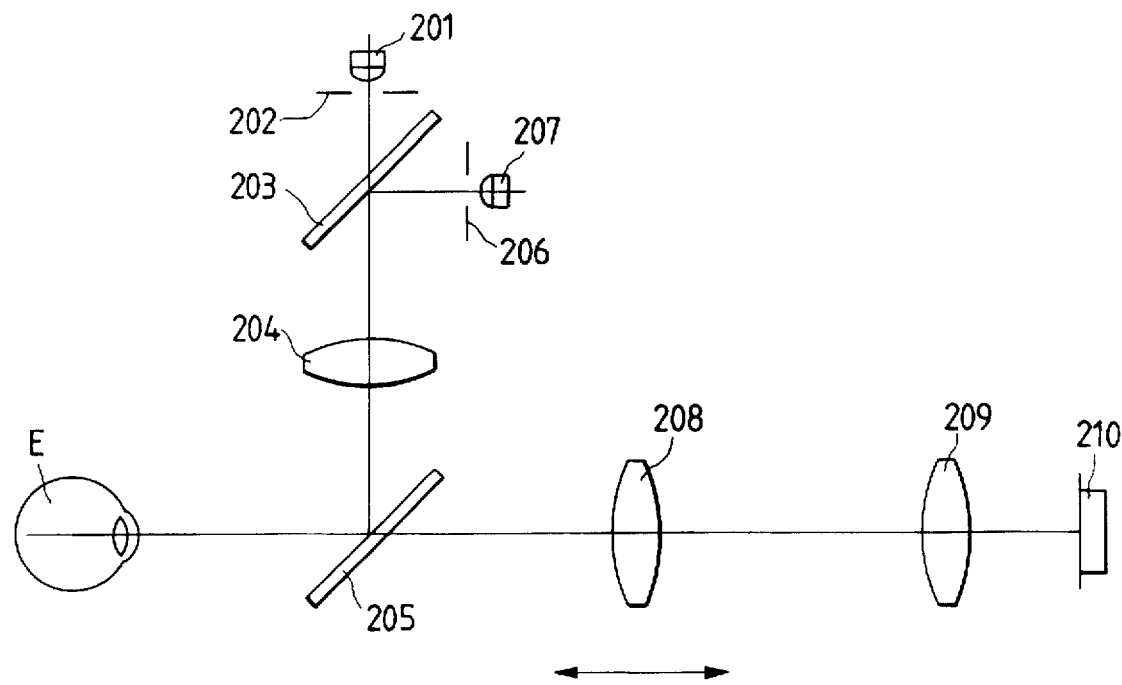
FIG. 30 is a schematic view of a ninth embodiment.

FIG. 30 is a schematic view of a ninth embodiment, wherein, on an optical path from a near-infrared light source 201 to the eye to be examined E, there are provided an aperture 202, a dichroic mirror 203, a lens 204, and a dichroic mirror 205, thus constituting an alignment optical system. On an optical path in the direction of reflection of the dichroic mirror 203 there are provided an aperture 206 and a light source 207 for retroillumination of the image, thus constituting a retroilluminating system, together with the dichroic mirror 203, lens 204 and dichroic mirror 205. Also on an optical path behind the dichroic mirror 205, there are provided an axially movable lens 208, a lens 209 and an imaging device 210 to constitute a retroillumination image observing optical system. The apertures 202, 207 are both positioned at the focal point of the lens 204. The dichroic mirror 203 has spectral characteristics of reflecting the infrared light while transmitting the near-infrared light, while the dichroic mirror 205 has spectral characteristics of transmitting a part of the near-infrared and longer-wavelength light.

The light beam from the light source 201 illuminates the aperture 202, then is guided through the dichroic mirror 203 and lens 204, then reflected by the dichroic mirror 205 and illuminates the anterior segment of the eye Ef. The reflected light beam therefrom is guided through the dichroic mirror 205, movable lens 208 and lens 209, and is focused as an image of the anterior segment on the imaging device 210. Also the light beam from the light source 207 illuminates the aperture 206, then is reflected by the dichroic mirror 203, then guided through, the lens 204 and reflected by the dichroic mirror 205 and illuminates the ocular fundus Er. The reflected light beam therefrom illuminates the pupil Ep, then is guided through the dichroic mirror 205, movable lens 208 and lens 209, and forms an image by retroillumination on the imaging device 210. The position of the movable lens 208, when the image of the anterior segment is formed by the light source 201 is formed on the imaging device 210, is taken as the original point, and there is determined the amount of movement of the movable lens 208 at the observation of the image by retroillumination.

Figure 31:
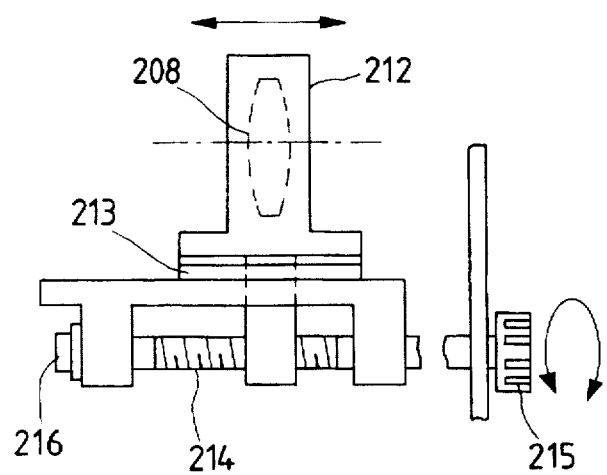
FIG. 31 is a schematic view of drive means for a movable lens.

FIG. 31 illustrates the driving means for the movable lens 208, wherein, under a lens support 212 supporting the movable lens 208 there is provided a sliding bearing parallel to the optical axis of the retroillumination image observing optical system. Therebelow provided is a screw rod 214 which is equipped, at the right-hand end, with an adjusting dial 215, and, at the left-hand end, with an encoder 216 for detecting the amount of movement of the optical system. Rotation of the adjusting dial 215 makes the screw rod 214 rotate so as to move the lens support 212 in a direction indicated by an arrow, and the encoder 216 detects the amount of movement of the retroillumination image observing optical system, from the rotation angle of the screw rod 214.

Figure 32:
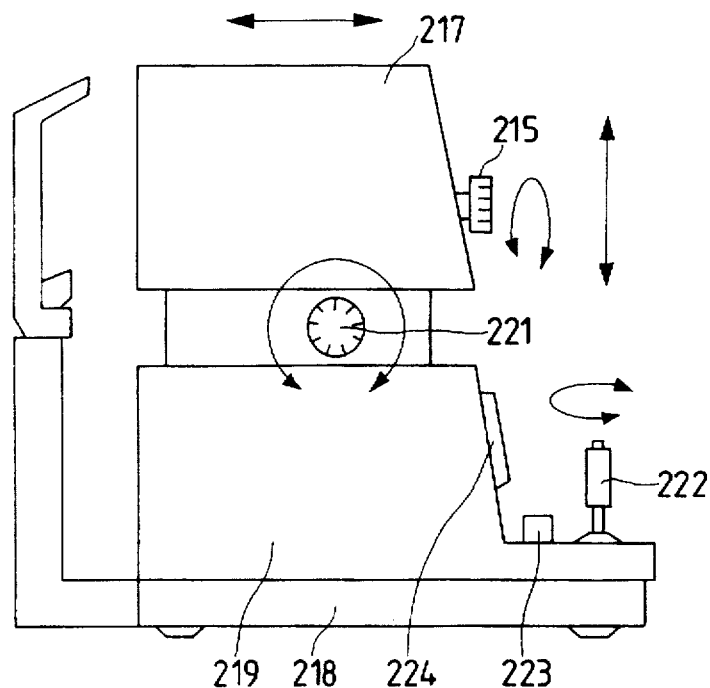
FIG. 32 is a schematic view of a tenth embodiment.

The optical system shown in FIG. 30 is disposed in an observation unit 217 shown in FIG. 32, which is placed on a stage 219 mounted on a fixed table 218 so as to be capable of parallel displacement. The observation unit 217 is equipped with the adjusting dial 215, and the stage 219 is provided with an adjusting dial 221, an operating rod 222 and a locking mechanism 223. The fixed table 218 is equipped with a television monitor 224.

A movement of the operating rod 222 in front, rear or lateral direction causes a corresponding sliding motion of the observation unit 217 together with the stage 219, relative to the fixed table 218. The stage 219 can be fixed by the fixed table 218, by means of the locking mechanism 223.

The vernier adjustment in the observation of the image by retroillumination and at the alignment is achieved by the movement of the observation unit 217, by the rotation of the adjusting dial 215 for the movement in front and back or the adjusting dial 221 in the lateral directions. The moving mechanism for the observation unit 217 by the adjusting dial 221 is basically same as the driving means for the movable lens 208 by the dial 215 shown in FIG. 31, except that the lens support 212 is replaced by the observation unit 217. Also rotation of the operating rod 222 moves the observation unit 217 in the vertical direction, for example by a mechanism known in the conventional auto refractometer. In the axial direction of the adjusting dial 221 and the operating rod 222, there are provided unshown encoders for detecting the amount of movement of the cornea observing system.

Figure 33:
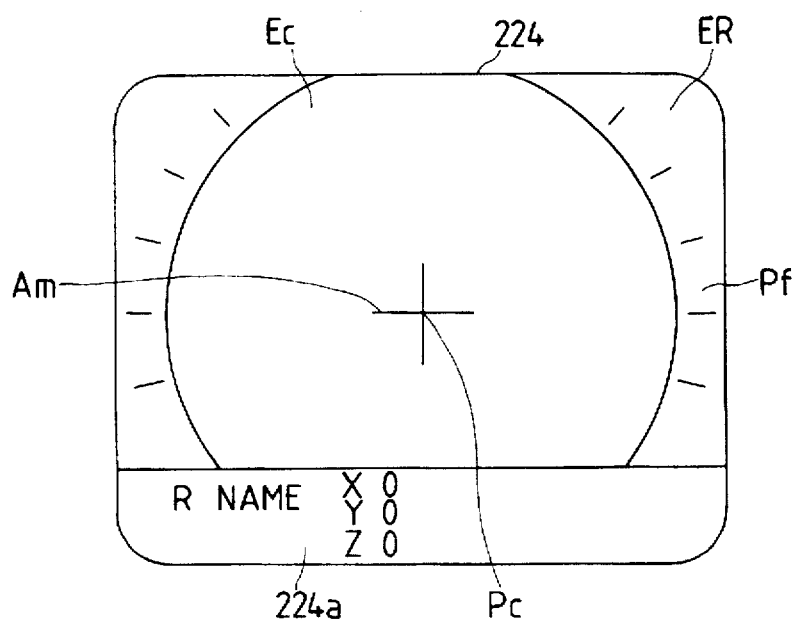
FIG. 33 is a schematic view of an image of the anterior segment of the eye, displayed on the television monitor.

When the light source 201 is turned on, an image Pf of the anterior segment of the eye is formed on the imaging device 210 whereby the image Pf consisting of the cornea Ec and the sclera Ek as shown in FIG. 33 is displayed on the monitor 224. A spot image Pc at the center of the cornea Ec is the reflected image of the aperture 202 formed by the cornea Ec.

The examiner executes the alignment by observing the monitor 224. In this state the light source 207 for retroillumination is turned off. At first the operating rod 222 is moved toward front or rear or in the lateral direction to move the observation unit 217 together with the stage 219, thereby focusing the spot image Pc to a certain extent. Then the stage 219 is fixed to the fixed table 218 by the locking mechanism 223, whereby the observation unit 217 is prevented from movement in the frontward, rearward or lateral direction. On the monitor 224 there are displayed, as shown in FIG. 33, the image Pf of the anterior segment of the eye consisting of the cornea Ec and the sclera Ek, the spot image Pc and a cross-shaped alignment mark Am at the center of the cornea Ec, and the name of the patient and etc. in a display area 224a.

The vernier adjustment of the observation unit 217 is conducted, in the vertical and horizontal directions, in such a manner that the spot image Pc coincides with the center of the cross-shaped alignment mark Am, and, in the axial direction, in such a manner that the corneal reflected image Pc becomes smallest. The photocurrent information of the corneal reflected image Pc on the imaging device 210 is continuously taken into the image memory as the video signal, and the completion of the precise alignment can be identified from the information.

In the video signal of the corneal reflected image Pc in the image memory, the completion of alignment is identified, in the vertical and horizontal directions, when the coordinate of the areal center of gravity of the dots exceeding a threshold level, which is selected slightly lower than the peak voltage level when the infocus state is reached, coincides with a designated coordinate, and, in the axial direction, when the number of dots exceeding the threshold level becomes maximum, and the position is detected by the signals from the encoders provided on the adjusting dials 215, 221 and the operating rod 222.

The position of the support member in this state is taken as the reference position, and the amounts of movement of the movable lens 208 and the observation unit 217 are calculated by the rotation angles of the adjusting dials 215, 221 and of the operating rod 222. The display area 234a of the monitor 224 displays the amounts of movement in the lateral, vertical and axial directions respectively as the X, Y and Z coordinates, taking the reference position as the original point.

Figure 34:
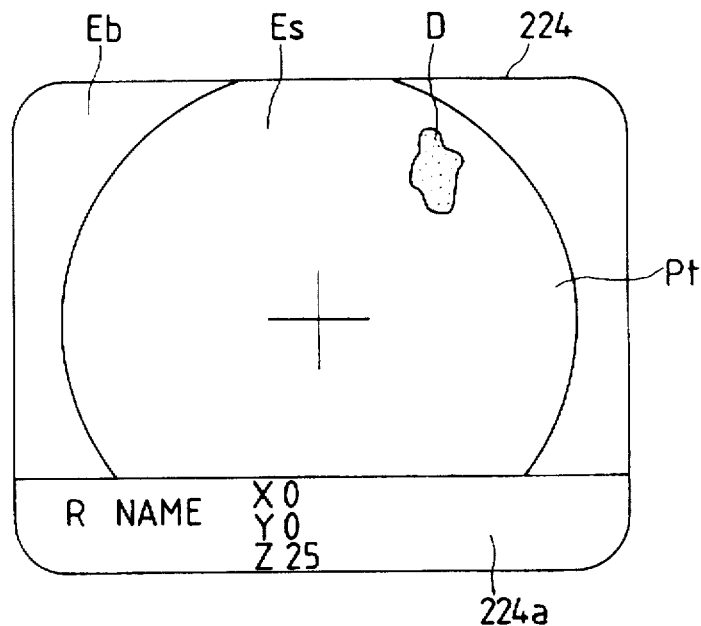
FIG. 34 is a schematic view of an image formed by retroillumination, displayed on the television monitor.
Figure 35:
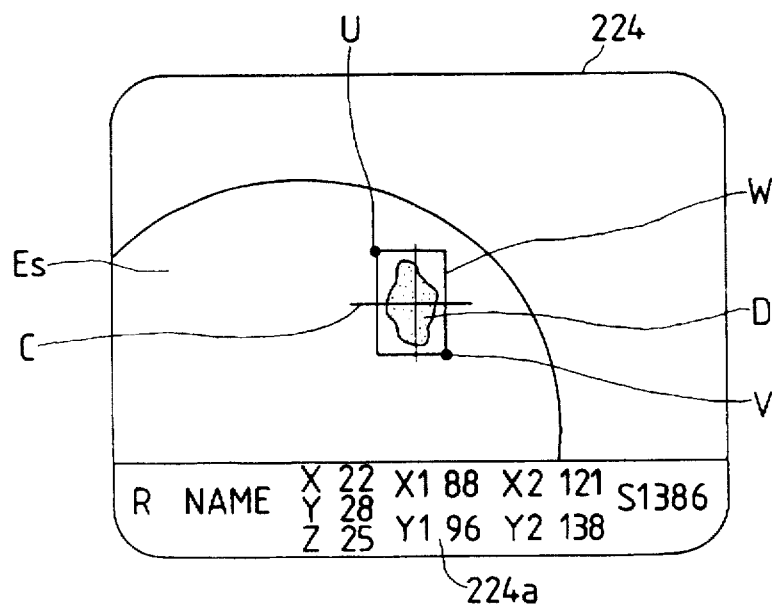
FIG. 35 is a schematic view of a binarized image formed by retroillumination, displayed on the television monitor.

When the alignment with the light source 201 is completed, the display area 224a displays the original points of the coordinates X, Y, Z. Then the light source 207 is activated to form the image Pt by retroillumination on the imaging device 210, whereby the image Pt by retroillumination, including the lens Es and the iris Eb as shown in FIG. 34 is displayed on the monitor 224. The examiner focuses the image Pt by turning the dial 215, while observing the monitor 224. If the lens Es contains an opacity area D, in order to determine the area thereof, a fine adjustment is executed with the dial 221 and the operating rod 222 in such a manner that the opacity area D reaches the center of the display field, as shown in FIG. 35. In this operation, since the position of the opacity area D may vary by the adjusting power of the eye to be examined E itself, the resolution is preferably reduced, but it is also possible to increase the resolution to the limits of the encoders.

Then an area calculating mode is adopted by the actuation of an unshown switch, whereby the image Pt by retroillumination on the monitor 224 is converted into a binarized image shown in FIG. 35, and a cross-shaped cursor flashes. At first a starting point U is moved in the vertical and horizontal directions by the operating rod 222, and the position of the starting point U is determined by an unshown push-button. Then an end point V flashes at the center of the cursor C, and the position of the end point V is determined in a same procedure. Thus a frame W, having the points U, V at the diagonal points, is determined, and the number of dots of the voltage O within the frame W is displayed, as the area S of the opacity portion D, in the display area 224a of the monitor 224. The coordinates X1, Y1, X2, Y2 of the start and end points U, V are displayed at the determination of the frame W.

For an eye to be examined E showing cataract, an image showing the image Pt by retroillumination together with the three-dimensional position of the opacity area D and the area S of the binarized opacity portion D may be recorded for example by a video printer, in order to enable time-dependent comparison of the opacity area D in a later observation of the same position.

In the observation of the image by retroillumination, the axial fine adjustment by the movement of the movable lens 208 results in a variation of the F-number thereof, depending on the position thereof. It is therefore preferable to move the movable lens 208 to the end of stroke toward the imaging device 210 by means of the adjusting dial 215, then to activate the encoder 216 and to vary the threshold level by the feedback of the subsequent rotation angle. However, such operation is not required in case the axial fine adjustment is conducted by the movement of the observation unit 217.

As explained in the foregoing, the ophthalmic measuring apparatus of the first invention allows to vary the illuminating amount of light of the light source for illuminating the anterior segment of the eye when the light source for illuminating the ocular fundus is turned on, whereby it is rendered possible to select the simultaneous observation of the image of the anterior segment of the eye and the image by retroillumination, or the observation of the only image by retroillumination.

In the ophthalmic apparatus of the second invention, the measuring light source is turned off when the lighting time of the light source for illuminating the ocular fundus becomes long.

In the ophthalmic measuring apparatus of the third invention, the image signal from the imaging device provided in the pupil observing system is memorized, whereby the memorized image of the pupil area can be supplied to an external equipment.

In the ophthalmic apparatus of the fourth invention, when the light source for illuminating the ocular fundus is turned on, the amount of the light beam reflected at the ocular fundus is detected at the pupil, so that there can be achieved various controls such as to enable observation by retroillumination with a constant illumination intensity.

In the ophthalmic apparatus of the fifth invention, the area of the ocular fundus illuminated by the light source is rendered variable, whereby there can be achieved an effect of enabling bright illumination of the pupil through the control of the light beam reflected at ocular fundus for illuminating the pupil, thereby facilitating the observation by retroillumination.

In the ophthalmic measuring apparatus of the sixth invention, the refractive power of the eye is continuously measured during the observation of the illuminated pupil, so that the measurable portion in the ocular fundus can be easily searched, with the confirmation of proper measured value of the refractive power of the eye and with the observation of the pupil by retroillumination. Consequently the refracive power of the eye to be examined can be easily measured even if the eye shows cataract.

In the ophthalmic measuring apparatus of the seventh invention, if the error is repeated in the measurement or if the reflected image of the ocular fundus or the image of the pupil area illuminated by the light beam reflected by the ocular fundus is abnormal or if the calculated refractive power is abnormal, the reflected image of the ocular fundus and/or the image of the pupil area is displayed together with the image of the anterior segment of the eye, whereby the examiner can easily identify the cause of the error in the measurement and can identify the portion and level of cataract particularly through the observation of the image of the pupil by retroillumination.

In the ophthalmic measuring apparatus of the eigth invention, the magnification of observation in the retroillumination image observing means is selected larger than that of the anterior segment of the eye observing means, thereby improving the operability in alignment and enabling the observation of the image by retroillumination in a magnified manner.

In the ophthalmic apparatus of the ninth invention, the illuminating light is projected to the eye to be examined and the lens is illuminated by the light reflected by the ocular fundus to achieve observation of the image by retroillumination. The retroillumination image observing optical system effects alignment utilizing a reference position for detecting the amount of movement of the optical system with respect to the eye to be examined and another position by means of a fine adjusting mechanism, and displays the detected amount of movement of the optical system. Thus a precise alignment to the observing position of the image by retroillumination can be easily achieved, even with an observing optical system of a high magnification with a small depth of focus.

What is claimed is:

1. An ophthalmic measuring apparatus comprising:
   an eye measuring system for projecting a measuring light beam onto the ocular fundus of an eye to be examined, including a detector for detecting the reflected light of the measuring light beam reflected from the ocular fundus of the eye, wherein predetermined information of the eye to be examined is measured on the basis of the detection of said reflected light beam by said detector;
   an observing system for enabling observation of the eye to be examined by an examiner;
   an anterior segment illuminating system for illuminating the anterior segment of the eye for observation of the anterior segment of the eye by said observing system;
   an ocular fundus illuminating system for illuminating the ocular fundus of the eye to be examined through the pupil thereof, and enabling observation, by said observing system of the pupil area of the eye to be examined, wherein the pupil area is illuminated by the reflected light from the ocular fundus of the eye illuminated by said ocular fundus illuminating system; and
   a control system for rendering variable the illumination intensity of said anterior segment illuminating system when the illumination by said ocular fundus illuminating system is conducted during the observation by said observing system.

2. An apparatus according to claim 1, wherein a refractive power of the eye is measured by said eye measuring system, as the predetermined information of the eye to be examined.

3. An apparatus according to claim 1, wherein said eye measuring system and said ocular fundus illuminating system use a common light source to respectively project and illuminate the ocular fundus with the measuring light beam.

4. An apparatus according to claim 1, wherein the peak of the wavelength spectrum of the measuring light beam is within the infrared spectral region.

5. An ophthalmic apparatus comprising:
   an observing system for enabling observation of an eye to be examined by an examiner;
   an ocular fundus illuminating system for illuminating the ocular fundus of the eye to be examined through the pupil thereof, and enabling observation, by said observing system, of the pupil area of the eye to be examined, wherein the pupil area is illuminated by the reflected light from the ocular fundus illuminated by an ocular fundus illuminating system;
   a time measuring system for measuring the illuminating time of the ocular fundus illuminating system; and
   a control system for terminating the illumination by the ocular fundus illuminating system when the illumination become longer than a predetermined time of the basis of the measurement by said time measuring system.

6. An apparatus according to claim 5, further comprising an eye measuring system wherein the refractive power of the eye to be examined is measured with said eye measuring system.

7. An apparatus according to claim 5, further comprising an eye measuring system for detecting predetermined information of the eye to be examined by projecting a measuring light beam onto the eye to be examined and detecting a returning light beam from eye to be examined, wherein the peak of the wavelength spectrum of the detecting light beam is in the infrared spectral region.

8. An ophthalmic apparatus comprising:

an observing system for enabling observation of an examined eye by an examiner, said observing system having imaging means for obtaining an image of the pupil of the examined eye for observation;

an ocular fundus illuminating system for illuminating the ocular fundus of the eye to be examined through the pupil thereof, and enabling observation, by said observing system, of the pupil area of the eye to be examined which is illuminated by the reflected light from the ocular fundus of the eye illuminated by said ocular fundus illuminating system;

detecting means for obtaining information of the light intensity, in the pupil of the eye to be examined, of the reflected light outgoing from the ocular fundus of the eye illuminated by said ocular fundus illuminating system, said detecting means obtaining the information of the light intensity in the pupil by judging the image of the pupil illuminated by the reflected light obtained by said imaging means; and measuring means for measuring predetermined information of the eye to be examined, by detecting measurement light from the eye to be examined via an optical path branched off from an optical path of said observing system.

9. An apparatus according to claim 8, further comprising control means for varying the light intensity of said measuring light beam on the basis of the information obtained from said detecting means.

10. An apparatus according to claim 8, wherein said observing system includes imaging means comprising image pick up means for producing data representing the image of the pupil area of the eye to be examined, and further comprising control means for varying the amplification factor of said image pickup means on the basis of the information obtained from said detection means.

11. An apparatus according to claim 8, wherein the refractive power of the eye is measured by said measuring means.

12. An apparatus according to claim 8, wherein the peak of the wavelength spectrum of the measurement light is in the infrared spectral range.

13. An ophthalmic apparatus comprising:

an observing system for enabling observation of an eye to be examined by an examiner;

an ocular fundus illuminating system for illuminating the ocular fundus of the eye to be examined through the pupil thereof, and enabling observation of the pupil area of the eye to be examined which is illuminated by the reflected light outgoing from the ocular fundus of the eye illuminated by said ocular fundus illuminating system with said observing system; and an illumination area varying system for varying the area of the ocular fundus of the eye to be illuminated by said ocular fundus illuminating system.

14. An apparatus according to claim 13, further comprising an eye measuring system, wherein the refractive power of the eye is measured by said eye measuring system.

15. An apparatus according to claim 13, further comprising an eye measuring system for detecting predetermined information of the eye to be examined by projecting a measuring light beam to the eye to be examined and detecting the returning light from said eye to be examined, wherein the peak of the wavelength spectrum of the measuring light beam is in the infrared spectral range.

16. An ophthalmic measuring apparatus comprising:

an eye measuring system for projecting a measuring light beam onto the ocular fundus of an eye to be examined including a detector for detecting the reflected light bema of the measuring light beam outgoing from the ocular fundus of the eye and measuring predetermined information of the eye to be examined on the basis of the detection of said reflected light beam by said detector;

an observing system for enabling observation of the eye to be examined by an examiner;

an ocular fundus illuminating system for illuminating the ocular fundus of the eye to be examined through the pupil thereof, and enabling observation of the pupil area of the eye to be examined which is illuminated by the reflected light outgoing from the ocular fundus of the eye illuminated by said ocular fundus illuminating system with said observing system; and control system for controlling said said eye measuring system to measure the predetermined information of said eye to be examined during observation by said observing system of the pupil area of the eye to be examined which is illuminated by said ocular fundus illuminating system.

17. An apparatus according to claim 16, wherein said eye measuring system employs measurement utilizing the illuminating light from said ocular fundus illuminating system as the measuring light beam.

18. An apparatus according to claim 16, wherein the refractive power of the eye is measured by said eye measuring system, as the predetermined information of the eye to be examined.

19. An apparatus according to claim 16, wherein the peak of the wavelength spectrum of the measuring light beam is within the infrared spectral range.

20. An ophthalmic measuring apparatus for use with an eye measuring system for projecting a measuring light beam onto the fundus of an eye to be examined, and including a first detector for detecting the measuring light beam reflected from the fundus of the eye, a first memory unit for storing image information from the first detector, and a calculation process circuit for calculating predetermined information of the eye to be examined on the basis of the image information stored in the first memory unit, wherein said apparatus comprises:

a display unit for displaying the anterior segment of the eye to be examined for observation;

an ocular fundus illuminating system for illuminating the fundus of the eye to be examined through the pupil thereof;

a second detector for detecting as an image the pupil area of the eye to be examined which is illuminated by the reflected light outgoing from the fundus of the eye illuminated by said ocular fundus illuminating system;

a second memory unit for storing the image information from said second detector; and a control system for causing said display means to display either or both of the image information stored in said first and second memory units, in case the calculation by the calculation process circuit shows an abnormality consecutively for a predetermined number of times of calculating the predetermined information.

21. An apparatus according to claim 20, wherein said control system includes first determining means for determining the presence or absence of an abnormality by image processing of the image information stored in the first memory unit, second determining means for determining the presence or absence of an abnormality by image processing of the image information stored in said second memory unit, and third determining means for determining the presence or absence of an abnormality in the output of the calculation process circuit, and wherein said control system causes said display unit to display either or both of the image information stored in said first and second memory unit, together with the image of the anterior segment of the eye to be examined according to the results of determination of said first, second, and third determining means.

22. An apparatus according to claim 20, wherein said control system includes an input unit for starting the measurement of the predetermined information of the eye to be examined by said eye measuring system, and wherein said control system is adapted, in response to an input signal from said input unit, to terminate the display of either or both of the image information of said first and second memory units by said display unit.

23. An apparatus according to claim 20, wherein a refractive power of the eye is measured, by said eye measuring system, as the predetermined information of the eye to be examined.

24. An apparatus according to claim 20, wherein the peak of the wavelength spectrum of the measuring light beam is within the infrared spectral range.

25. An ophthalmic measuring apparatus comprising:

an eye measuring system for detecting predetermined information of an eye to be examined by projecting a measuring light beam to the eye to be examined and detecting the returning light from the eye to be examined;

an ocular fundus illuminating system for illuminating the ocular fundus of the eye to be examined through the pupil thereof by a first light source;

a retroillumination observation system for guiding the reflected light from the ocular fundus illuminated by said ocular fundus illuminating system and enabling observation of the image by retroillumination of the lens of the eye to be examined;

an anterior segment of the eye illuminating system for illuminating the anterior segment of the eye to be examined by a second light source different from said first light source;

an anterior segment of the eye observing system for guiding the reflected light from the anterior segment of the eye illuminated by said anterior segment of the eye illuminating system and enabling observation of the anterior segment of the eye to be examined;

a light source switching unit for turning off said first light source during the observation of the anterior segment of the eye by said anterior segment of the eye observing system, and turning on first light source during the observation of the image by retroillumination by said retroillumination observation system; and an observation magnification setting system for setting the magnification of observation by said retroillumination observation system larger than that of said anterior segment of the eye observing system.

26. An apparatus according to claim 25, wherein said retroillumination observation system and said anterior segment of the eye observing system have a common optical system, and said observation magnification setting system is adapted to vary, in the observation of the anterior segment of the eye by said anterior segment of the eye observing system and in the observation of the image by retroillumination by said retroillumination observation system, the magnification of observation by an electric zooming method.

27. An apparatus according to claim 25, wherein said retroillumination observation system and said anterior segment of the eye observing system are composed at least partly of different optical element, and said observation magnification setting system includes optical path switching means and is adapted to vary the magnification of observation, by switching the optical path utilizing said optical path switching means, in the observation of the anterior segment of the eye by said anterior segment of the eye observing system and in the observation of the image by retroillumination by said retroillumination observation system.

28. An apparatus according to claim 25, further comprising a cornea shape measuring system, which has a common optical system with said retroillumination observation system.

29. An apparatus according to claim 28, wherein said retroillumination observation system and said anterior segment of the eye observing system have a common optical system, and said observation magnification setting system is adapted to vary the magnification of observation by varying at least an optical element in said apparatus, in the observation of the anterior segment of the eye by said anterior segment of the eye observing system and in the observation of the image by retroillumination by said retroillumination observation system.

30. An ophthalmic apparatus comprising:

an ocular fundus illuminating system for illuminating the fundus of an eye to be examined through the pupil thereof;

a retroillumination observation system for guiding the reflected light from the fundus of the eye illuminated by said ocular fundus illuminating system, and enabling observation of the image by retroillumination of the lens of the eye to be examined;

alignment means for aligning said retroillumination observation system respectively with a reference position on the eye to be examined and with a specified portion of the eye to be examined different from the reference position; and a displacement detecting unit for detecting the amount of relative displacement of said retroillumination observation system when said retroillumination observation system, by said alignment means, is aligned with the reference position and with the specified portion of the eye different from the reference position.

31. An apparatus according to claim 30, wherein said alignment means includes a reference position auto detecting unit for detecting the reference position, and said displacement detecting unit functions in accordance with the reference position detected by said reference position auto detecting unit.

32. An apparatus according to claim 31, wherein said reference position auto detecting unit is adapted to project a light beam onto the eye to be examined, to receive the corneal reflected light from said eye to be examined by a photosensor and to detect the reference position from the area and intensity of the light on said photosensor.

33. An apparatus according to claim 30, further comprising area calculating means for calculating an approximate area of the specified portion of the eye to be examined, aligned with said retroillumination observation system by said alignment means.

34. An apparatus according to claim 33, wherein said area calculating means includes an image memory for storing the image illuminated by retroillumination in a binarized state, and designation means for designating, by a frame, an area containing the specified portion of the eye to be examined in a binarized still image in said image memory, and wherein said area calculating means is adapted to calculate the number of dots of the specified portion within the frame as an area.

35. An ophthalmic apparatus comprising:

an observing system for enabling observation of an examined eye by an examiner;

an ocular fundus illuminating system for illuminating the ocular fundus of the eye to be examined through the pupil thereof, and enabling observation, by said observing system, of the pupil area of the eye to be examined which is illuminated by the reflected light outgoing from the ocular fundus of the eye illuminated by said ocular fundus illuminating system;

detecting means for detecting the light intensity, in the pupil of the eye to be examined, of the reflected light outgoing from the ocular fundus of the eye illuminated by said ocular fundus illuminating system; and control means for varying the illumination by said ocular fundus illuminating system on the basis of the detection by said detecting means.

36. An apparatus according to claim 35, wherein said observing system comprises an imaging device, and wherein said detecting means detects the light intensity in the pupil on the basis of the data obtained from said imaging device.

37. An apparatus according to claim 36, further comprising an eye measuring system for detecting predetermined information of the eye to be examined by detecting light from the eye to be examined via an optical path branched off from an optical path of said observing system.

* * * * *

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COVER PAGE

[56] References Cited,
      "2302243 12/1990 Japan" should read --2-302243 12/1990 Japan--, and "496730 3/1992 Japan" should read --4-96730 3/1992 Japan--.

COLUMN 1,
Line 28, "project" should read --projects--.
Line 37, "occurred happens" should read --occur--.
Line 38, "an" should read --the--.
Line 41, "designed" should read --designed to be--, and "generally" (second occurrence) should read --generally using a--.
Line 46, "Also the" should read --Also,--.
Line 52, "the" should be deleted.
Line 65, "Also should read --Also,--.

COLUMN 2,
Line 5, "wavelength of" should be deleted, and "light source 1 and" should read --light source 1, (i.e., a wavelength thereof) and--.
Line 6, "the rest part of wavelength thereof." should read --the rest thereof, (i.e., a different wavelength).--.
Line 15, "then" should read --is then--.
Line 16, "and" should read --and is--.
Line 23, "annular" should read --annulus--.
Line 33, "arts" should read --art--.
Line 34, "is" should read --is designed--, and "a" should read --an--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 2 (CONT.),
Line 35, "in the"(2nd occurrence) should read --to provide an--.
Line 38, "The object of a first" should read --A first object of the--.
Line 43, "The object of a second" should read --A second object of the--.
Line 46, "hazard" should read --hazards--.
Line 47, "The object of a third" should read --A third object of the--.
Line 50, "for output to an" should read --for outputting to--.
Line 51, "The object of a fourth" should read --A fourth object of the--.
Line 55, "The object of a fifth" should read --A fifth object of the--.
Line 56, "the" should be deleted.
Line 59, "The object of a sixth" should read --A sixth object of the--.
Line 62, "measuring" should read --measuring a--.
Line 65, "shows" should read --has a--.
Line 66, "The object of a seventh" should read --A seventh object of the--.

COLUMN 3,
Line 1, "failure" should read --failure of--.
Line 2, "the" (first occurrence) should be deleted.
Line 4, "shows" should read --has a--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

Page 3 of 14

It is certified that error appears in the above-identified patent and that said Letters Patent is hereby corrected as shown below:

COLUMN 3 (CONT.),
Line 5, "The object of an eighth" should read --An eighth object of the--.
Line 12, "The object of a ninth" should read --A ninth object of the--.
Line 18, "apparatus" should read --apparent--,
Line 19, "embodiments" should read --embodiments discussed below--.
Line 22, "shown" should be deleted.
Line 31, "elevation" should read --elevational--.
Line 38, "retractomery" should read --refractometry--.
Line 42, "are" should read --which are--.
Line 54, "1/4," should read --1/4 normal size,--.
Line 56, "are" should read --which are--.
Line 62, "1/4," should read --1/4 normal size,--.
Line 66, "1/4," should read --1/4 normal size--.

COLUMN 4,
Line 7, " elevation" should read --elevational--.
Line 39, "a holed mirror 26," should read --a mirror 26 containing a hole,--.
Line 41, "holed" should be deleted.
Line 43, "six," should read --six--.
Line 47, "along" should read --movable along--.
Line 54, "segment." should read --segment of the eye.--.
Line 58, "of reflecting the" should read --so as to reflect--.
Line 59, "transmitting the" should read --transmit--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 4 (CONT.),
Line 62, "wavelength" should read --wavelength thereof,--, and "of reflecting the" should read --to reflect--.
Line 65, "reflecting" should read --reflecting a certain proportion of--.
Line 66, "light source 21 by a certain proportion," should read --light source 21,--.

COLUMN 5,
Line 2, "illuminates" should read --illuminate--.
Line 11, "then" should read --is then--.
Line 23, "holed" should be deleted.
Line 28, "holed" should be deleted.
Line 34, "calculate d" should read --calculated--.
Line 48, "f or" should read --for--.
Line 53, "connected," should read --connected--.

COLUMN 6,
Line 17, "Also in consideration of the protection of" should read --Also, to protect--.
Line 21, "the" should be deleted.
Line 26, "at the" should read --for--.
Line 36, "at" should read --for measuring--.
Line 46, "eye" should read --eye,--.
Line 46, "eyelid and the image" should read --the eyelid,--.
Line 55, "effects controls such as" should read --controls the--.
Line 64, "difficult" should read --difficult to perform--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 6 (CONT.),
Line 65, "a" should be deleted.
Line 66, "of" (first occurrence) should read --of a--.

COLUMN 7,
Line 1, "of amount" should read --of light--.
Line 3, "the" (first occurrence) should be deleted.
Line 6, "to" should read --than--.
Line 7, "Ep" should read Ep,--.
Line 8, "an" should be deleted.
Line 9, "Consequently" should read --Consequently,--.
Line 25, "holed" should read --hole-containing--.
Line 27, "holed" should read --hole-containing--.
Line 49, "then" should read --is then--, and "projected" should read --is projected--.
Line 55, "aperture 54," should read --the aperture 54,--.
Line 56, "lens" should read --the lens--, and "dichroic" should read --the dichroic--.
Line 61, "holed" should read --hole-containing--.
Line 62, "lens" should read --the lens--, and "splitting" should read --the splitting--.

COLUMN 8,
Line 36, "for" should be deleted.
Line 63, "opacity," should read --opacity of the eye,--.

COLUMN 9,
Line 8, "part" should be deleted.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 9 (CONT.),
Line 11, "aligns in a part" should read --performs alignment in a part of the eye--.
Line 11, "opacity." should read --opaque portion.--.
Line 12, "enabling" should read --which enables the user to perform--.
Line 18, "accommodation of" should read --so that--.
Line 19, "Thus" should read --Thus,--.
Line 25, "refractive" should read --refractive observation--.
Line 27, "but" should read --and--.
Line 32, "in" should read --in an--.
Line 41, "there" should read --in that there--.
Line 46, "then" should read --is then--.
Line 64, "that" should read --in that--.
Line 66, "and" should read --and is--.

COLUMN 10,
Line 3, "and" (1st occurrence) should read --and is--.
Line 4, "reflected" should read --is reflected--, and "and" should read --and is--.
Line 6, "forth" should read --fourth--.
Line 7, "opacity" should read --opaque portion--.
Line 8, "opacity" should read --opaque portion--.
Line 14, "holed" should read --hole-containing--.
Line 16, "hole" should read --hole-containing--.
Line 35, "of transmit-" should read --so that it transmits--.

UNITED STATES PATENT AND TRADEMARK OFFICE
CERTIFICATE OF CORRECTION

PATENT NO. : 5,751,396

DATED : May 12, 1998

INVENTOR(S) : TAKASHI MASUDA, ET AL.

It is certified that error appears in the above-identified patent and that said Letters Patent is hereby corrected as shown below:

COLUMN 10 (CONT.),
Line 36, "ting" should be deleted, and "reflecting" should read --reflects--.
Line 63, "of which" should read --whose--.
Line 66, "of which" should read --whose--.

COLUMN 11,
Line 7, "then" should read --is then--.
Line 8, "and" should read --and is--.
Line 32, "holed" should read --hole-containing--.
Line 38, "holed" should read --hole-containing--.
Line 44, "then" should read --is then--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 12,
Line 1, "opacity" should read --opaque--.
Line 3, "In" should read --During--.
Line 3, "refractometry," should read --refractometry measurement,--.
Line 8, "and" should read --and adjusts the--.
Line 10, "AR" should read --Ar--.
Line 33, "displayed" should read --displayed an indication--.
Line 38, "Then" should read --Then,--.
Line 39, "the" should be deleted.
Line 41, "increased" should read --incremented--.
Line 42, "image" should read --images--.
Line 44, "1/4" should read --1/4 normal size--.
Line 49, "1/4," should read --1/4 normal size,--.
Line 66, "at" should be deleted.
Line 67, "measuring" should read --measurement--.

COLUMN 13,
Line 1, "pressed is detected," should read --pressed,--.
Line 24, "the" (second occurrence) should read --there is--.
Line 25, "result indicates" should be deleted, and "the" should read --a--.
Line 26, "or" should read --or a--.
Line 37, "1/4," should read --1/4 normal size,--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

```
COLUMN 13 (CONT.)
Line 39, "Also" should read --Also,--.
Line 44, "is" should read --are--, and "to 128," should
read --to memory 128,--.
Line 45, "1/4," should read --1/4 normal,--.
Line 49, "314" should read --314 that an--.
Line 54, "to 128" should read --to image memory 128--,
and "1/4" should read --1/4 normal--.
Line 57, "At" should be deleted.
Line 58, "the step 316 the state that the measuring
switch 132 is" should read --Step 316 awaits pressing
of the measuring switch 132 and,--.
Line 59, "pressed is waited and," should be deleted.

COLUMN 14,
Line 5, "pressed is waited," should read --pressed,--.
Line 11, "error" should read --errors--.
Line 13, "in reduced manner in size to 1/4" should read
--at a reduced size of 1/4 normal--.
Line 20, "1/4," should read --1/4 normal,--.
Line 29, "Also" should read --Also,--.
Line 35, "then" should read --is then--.
Line 38, "then" should read --is then--.
Line 39, "focused" should read --is focused--.
```

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

<u>COLUMN 15</u>
Line 1, "opacity" should read --opaque--.
Line 3, "opacity" should read --opaque--.
Line 5, "opacity" should read --opaque--.
Line 6, "of" should read --of the image undergoing--.
Line 8, "further" should read --further,--.

Line 18, "holed" should read --hole-containing--.
Line 22, "Also" should read --Also,--.
Line 27, "holed" should read --hole-containing--.
Line 39, "directions" should read --orthogonal direction--.
Line 41, "Also" should read --Also,--.

<u>COLUMN 16</u>,
Line 4, "holed" should read --hole-containing--.
Line 5, "and" should read --and the--.
Line 9, "holed" should read --hole-containing--.
Line 25, "then" should read --is then--.
Line 26, "and" should read --and is--.
Line 32, "target" should read --the target--.
Line 33, "relay lens 154 aperture 155, aperture" should read --the relay lens 154, the aperture 155, the aperture--.
Line 34, "holed" should read --hole-containing--.
Line 35, "objective" should read --the objective--.
Line 37, "relay" should read --the relay--, and "light" should read --the light--.
Line 38, "field lens 178, mirror 179, relay lens" should read --the field lens 178, the mirror 179, the relay lens 180,--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 16 (CONT.),
Line 39, "aperture 182 and" should read --the aperture 182 and the--.
Line 57, "example" should read --example,--.
Line 60, "and," should read --and--.
Line 63, "is aberrated" should read --deviates--.
Line 64, "from the" should read --from a normal--.

COLUMN 17,
Line 16, "light" (both occurrences) should read --the light--, and "relay" should read --the relay--.
Line 17, "field" should read --the field--, "mirror" should read --the mirror--, and "relay" should read --the relay--.
Line 28, "target" should read --the target--.
Line 29, "relay" should read --the relay--, and "aperture" should read --the aperture--.
Line 30, "aperture" should read --the aperture--, "holed" should read --hole-containing--, and "light" should read --the light--.
Line 31, "objective" should read --the objective--.
Line 33, "then" should read --is then--.
Line 34, "then" should read --is then--, and "light" should read --the light--.
Line 35, "field (both occurrences) should read --the field--, and "mirror" should read --the mirror--.
Line 36, "synthesizing" should read --the synthesizing--.
Line 57, "then" should read --is then--.
Line 61, "then" should read --then is--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 18,
Line 1, "lens" should read --the lens--.
Line 41, "Also" should read --Also,--.
Line 43, "then" should read --then is--, "through," should read --through--, and "and" should read --and is--.
Line 46, "movable" should read --the movable--.
Line 47, "lens" should read --the lens--.

COLUMN 19,
Line 23, "Also" should read --Also,--.
Line 24, "example" should read --example,--.
Line 25, "refractometer." should read --refractometer art.--.
Line 32, "FIG. 33" should read --FIG. 33,--.
Line 44, "direction." should read --directions.--.
Line 47, "spot image Pc" should read --spot image Pc,--.
Line 49, "patient and etc." should read --patient, etc.,--.
Line 66, "selected" should read --selected to be--.

COLUMN 20,
Line 22, "opacity" should read --opaque--.
Line 25, "opacity" should read --opaque--.
Line 27, "opacity" should read --opaque--.
Line 40, "in a" should read --by the--, and "Thus" should read --Thus,--.
Line 42, "voltage O" should dread --voltage 0--.
Line 43, "opacity" should read --opaque--.
Line 47, "showing" should read --having a--.
Line 49, "opacity" should read --opaque--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 20 (CONT.),
Line 50, "opacity" should read --opaque--.
Line 52, "opacity" should read --opaque--.
Line 59, "of stroke" should read --of its stroke--.
Line 63, "such" should read --such an--, and "case" should read --case when--.
Line 67, "invention allows" should read --embodiment allows one--.

COLUMN 21,
Line 6, "the only image" should read --image only--.
Line 8, "invention," should read --embodiment,--.
Line 13, "invention," should read --embodiment,--.
Line 17, "invention," should read --embodiment,--.
Line 23, "invention," should read --embodiment,--.
Line 31, "invention," should read --embodiment,--.
Line 36, "Consequently" should read --Consequently,--.
Line 40, "invention," should read --embodiment,--, and "the error is repeated" should read --there is a repeated error--.
Line 49, "cataract" should read --the cataract,--.
Line 52, "invention," should read --embodiment,--.
Line 53, "selected" should read --selected to be--.

UNITED STATES PATENT AND TRADEMARK OFFICE
CERTIFICATE OF CORRECTION

PATENT NO. : 5,751,396
DATED : May 12, 1998
INVENTOR(S) : TAKASHI MASUDA, ET AL.

It is certified that error appears in the above-identified patent and that said Letters Patent is hereby corrected as shown below:

COLUMN 22,
Line 1, "Thus" should read --Thus,--.
Line 2, "to the observing" should read --of the observed--.
Line 58, "become" should read --becomes--.

COLUMN 23,
Line 2, "eye" should read --the eye--.

COLUMN 24,
Line 8, "bema" should read --beam--; and
Line 21, "said" (second occurrence) should be deleted.

SHEET 5 OF THE DRAWINGS
FIGURE 8, "SOURSE" should read --SOURCE--.

Signed and Sealed this

Twenty-eighth Day of September, 1999

Attest:

Q. TODD DICKINSON

*Attesting Officer*     *Acting Commissioner of Patents and Trademarks*